(12) United States Patent
Andoh et al.

(10) Patent No.: US 6,239,077 B1
(45) Date of Patent: May 29, 2001

(54) AMINOACETONITRILE DERIVATIVE AGRICULTURAL AND HORTICULTURAL INSECTICIDE CONTAINING THE SAME AND USE THEREOF

(75) Inventors: Nobuharu Andoh, Sakai; Osamu Sanpei; Kazuyuki Sakata, both of Kawachinagano, all of (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 0 days.

(21) Appl. No.: 09/295,319

(22) Filed: Apr. 21, 1999

(30) Foreign Application Priority Data

May 1, 1998 (JP) .................................................. 10-137806

(51) Int. Cl.$^7$ .......................... A01N 37/34; C07C 255/03
(52) U.S. Cl. ........................... 504/312; 558/392; 558/389
(58) Field of Search .................... 504/312, 141; 558/392, 389

(56) References Cited

U.S. PATENT DOCUMENTS

| | | | |
|---|---|---|---|
| 5,462,913 | 10/1995 | Fischer et al. | 504/138 |
| 5,504,057 | 4/1996 | Fischer et al. | 504/283 |
| 5,508,436 | 4/1996 | Fischer et al. | 548/544 |
| 5,602,078 | 2/1997 | Fischer et al. | 504/283 |
| 5,622,917 | 4/1997 | Fischer et al. | 504/283 |
| 5,672,718 | 9/1997 | Fischer et al. | 549/28 |
| 5,677,449 | 10/1997 | Fischer et al. | 544/165 |
| 5,847,211 | 12/1998 | Fischer et al. | 564/123 |

FOREIGN PATENT DOCUMENTS

| | | |
|---|---|---|
| 0 854 134 A1 | 7/1998 | (EP) . |
| 04198158 * | 7/1992 | (JP) . |

OTHER PUBLICATIONS

Shah, V. P. et al. : Synthesis and biological study of a series of S–substituted alpha–mercaptohippuramides and nitriles. J. med. Chem. vol. 14, pp. 456–458, 1971.*

J. Org. Chem. 763, 1948, Organic Synthesis Coll., vol. 1, 436.

J. Org. Chem. 763, 1948, Organic Synthesis Coll., vol. 1, 336.

Beilstens Handbuch 9, 573.

Beilstens Handbuch 9, 633, etc.

* cited by examiner

Primary Examiner—Charanjit S. Aulakh
(74) Attorney, Agent, or Firm—Oliff & Berridge, PLC

(57) ABSTRACT

An aminoacetonitrile derivative of the formula (I):

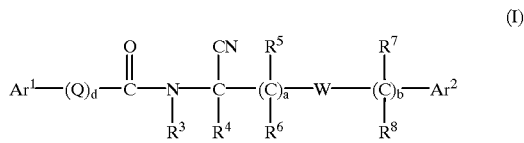

(wherein $Ar^1$ and $Ar^2$ represents phenyl group; substituted phenyl group having at least one subsituent selected from halogen atom, nitro group, cyano group, (halo) $C_1$–$C_6$ alkyl group, (halo) $C_1$–$C_6$ alkoxyl group, (substituted) pheny group, (substituted) phenyloxy group and (substituted) phenylacetylene group; (substituted) pyridyl group; and (substituted) naphthyl group, Q represents —C($R^1$)($R_2$)— (wherein $R^1$ and $R_2$ represent hydrogen atom, halogen atom, (halo) $C_1$–$C_6$ alkyl group, (halo) $C_1$–$C_6$ alkoxy group, (substituted) $C_3$–$C_6$ cycloalkyl group), or $R^1$ and $R^2$ may be bound to represent $C_2$–$C_6$ alkylene group), —CH═CH— or —C≡C—, d is 0 or an integer of 1, $R^3$ represents hydrogen atom, (halo) $C_1$–$C_6$ alkyl group, $R^4$, $R^5$, $R^6$, $R^7$ and $R^8$ represent hydrogen atom, halogen atom, (halo) $C_1$–$C_6$ alkyl group, W is —O—, —S—, —$SO_2$— or —N($R^9$)— (wherein $R^9$ is a hydrogen atom or $C_1$–$C_6$ alkyl group), and a and b are 0 or an integer of 1 to 4)), an agricultural and hortecultural insecticide containing as an active ingredient said derivative, and a method for using the insecticide.

11 Claims, No Drawings

AMINOACETONITRILE DERIVATIVE AGRICULTURAL AND HORTICULTURAL INSECTICIDE CONTAINING THE SAME AND USE THEREOF

BACKGROUND OF THE INVENTION

1. Field of the Invention

The present invention relates to an aminoacetonitrile derivative of the formula (I) and to an agricultural and horticultural insecticide containing the said derivative as an active ingredient. The present invention also relates to a method for using the insecticide.

2. Description of the Related Art

Japanese Patent Application Laid-open No. Hei 9-48750 (1997) discloses a phenylalkanoic acid amide derivative as an agricultural and horticultural fungicide, Japanese Patent Application Laid-open No. Hei 6-220004 (1994) discloses N-phenylacetaminonitriles as intermediates in production, and Japanese Patent Applications Laid-opens No. Hei 6-263731 (1994), No. Hei 6-271537 (1994) and No. Hei 7-252222 (1995) disclose compounds similar to the aminoacetonitrile derivative of the formula (I) of the present invention.

SUMMARY OF THE INVENTION

With view to developing novel agricultural and horticultural insecticide, the present inventors have made intensive research and as a result, they have now found that an aminoacetonitrile derivative of the formula (I) is a novel compound and has a remarkable insecticidal effect, thus completing the present invention.

DETAILED DESCRIPTION OF THE INVENTION

The present invention relates to an aminoacetonitrile derivative of the formula (I) and to an agricultural and horticultural insecticide containing said derivative as an active ingredient:

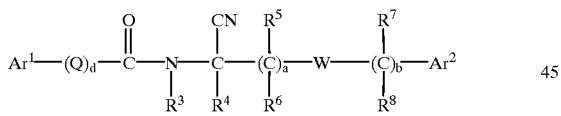

(I)

(wherein $Ar^1$ and $Ar^2$ may be the same or different and each represents a phenyl group;

a substituted phenyl group having at least one substituent which may be the same or different and selected from the group of a halogen atom, a nitro group, a cyano group, a $C_1$–$C_6$ alkyl group, a halo $C_1$–$C_6$ alkyl group, a $C_1$–$C_6$ alkoxy group, a halo $C_1$–$C_6$ alkoxy group, a $C_2$–$C_6$ alkenyl group, a halo $C_2$–$C_6$ alkenyl group, a $C_2$–$C_6$ alkynyl group, a $C_3$–$C_6$ cycloalkyl group, a $C_2$–$C_6$ alkenyloxy group, a halo $C_2$–$C_6$ alkenyloxy group, a $C_1$–$C_6$ alkylthio group, a halo $C_1$–$C_6$ alkylthio group, a $C_1$–$C_6$ alkylsulfonyloxy group, a halo $C_1$–$C_6$ alkylsulfonyloxy group, a $C_1$–$C_6$ alkylsulfinyl group, a halo $C_1$–$C_6$ alkylsulfinyl group, a $C_1$–$C_6$ alkylsulfonyl group, a halo $C_1$–$C_6$ alkylsulfonyl group, a $C_2$–$C_6$ alkenylthio group, a halo $C_2$–$C_6$ alkenylthio group, a $C_2$–$C_6$ alkenylsulfinyl group, a halo $C_2$–$C_6$ alkenylsulfinyl group, a $C_2$–$C_6$ alkenylsulfonyl group, a halo $C_2$–$C_6$ alkenylsulfonyl group, a $C_1$–$C_6$ alkylamino group, a di-$C_1$–$C_6$ alkylamino group, a $C_1$–$C_6$ alkylsulfonylamino group, a halo $C_1$–$C_6$ alkylsulfonylamino group, a $C_1$–$C_6$ alkylcarbonyl group, a halo $C_1$–$C_6$ alkylcarbonyl group, a $C_1$–$C_6$ alkyloxycarbonyl group, a phenyl group, a substituted phenyl group having at least one substituent which may be the same or different and selected from the group consisting of a halogen atom, a cyano group, a nitro group, a $C_1$–$C_6$ alkyl group, a halo $C_1$–$C_6$ alkyl group, a $C_1$–$C_6$ alkoxy group, a halo $C_1$–$C_6$ alkoxy group, a $C_1$–$C_6$ alkylthio group, a halo $C_1$–$C_6$ alkylthio group, a $C_1$–$C_6$ alkylsulfinyl group, a halo $C_1$–$C_6$ alkylsulfinyl group, a $C_1$–$C_6$ alkylsulfonyl group and halo $C_1$–$C_6$ alkylsulfonyl group, a phenyloxy group, a substituted phenyloxy group having on the ring thereof at least one substituent which may be the same or different and selected from the group consisting of a halogen atom, a cyano group, a nitro group, a $C_1$–$C_6$ alkyl group, a halo $C_1$–$C_6$ alkyl group, a $C_1$–$C_6$ alkoxy group, a halo $C_1$–$C_6$ alkoxy group, a $C_1$–$C_6$ alkylthio group, a halo $C_1$–$C_6$ alkylthio group, a $C_1$–$C_6$ alkylsulfinyl group, a halo $C_1$–$C_6$ alkylsulfinyl group, a $C_1$–$C_6$ alkylsulfonyl group and a halo $C_1$–$C_6$ alkylsulfonyl group, a phenylacetylene group, a substituted phenylacetylene group having on the ring thereof at least one substituent which may be the same or different and selected from the group consisting of a halogen atom, a cyano group, a nitro group, a $C_1$–$C_6$ alkyl group, a halo $C_1$–$C_6$ alkyl group, a $C_1$–$C_6$ alkoxy group, a halo $C_1$–$C_6$ alkoxy group, a $C_1$–$C_6$ alkylthio group, a halo $C_1$–$C_6$ alkylthio group, a $C_1$–$C_6$ alkylsulfinyl group, a halo $C_1$–$C_6$ alkylsulfinyl group, a $C_1$–$C_6$ alkylsulfonyl group and a halo $C_1$–$C_6$ alkylsulfonyl group, a pyridyloxy group and a substituted pyridyloxy group having on the ring thereof at least one substituent which may be the same or different and selected from the group consisting of a halogen atom, a cyano group, a nitro group, a $C_1$–$C_6$ alkyl group, a halo $C_1$–$C_6$ alkyl group, a $C_1$–$C_6$ alkoxy group, a halo $C_1$–$C_6$ alkoxy group, a $C_1$–$C_6$ alkylthio group, a halo $C_1$–$C_6$ alkylthio group, a $C_1$–$C_6$ alkylsulfinyl group, a halo $C_1$–$C_6$ alkylsulfinyl group, a $C_1$–$C_6$ alkylsulfonyl group and a halo $C_1$–$C_6$ alkylsulfonyl group;

a pyridyl group;

a substituted pyridyl group having on the ring thereof at least one substituent which may be the same or different and selected from the group consisting of a halogen atom, a cyano group, a nitro group, a $C_1$–$C_6$ alkyl group, a halo $C_1$–$C_6$ alkyl group, a $C_1$–$C_6$ alkoxy group, a halo $C_1$–$C_6$ alkoxy group, a $C_2$–$C_6$ alkenyloxy group, a halo $C_2$–$C_6$ alkenyloxy group, a $C_1$–$C_6$ alkylthio group, a halo $C_1$–$C_6$ alkylthio group, a $C_1$–$C_6$ alkylsulfinyl group, a halo $C_1$–$C_6$ alkylsulfinyl group, a $C_2$–$C_6$ alkenylthio group, a halo $C_2$–$C_6$ alkenylthio group, a $C_2$–$C_6$ alkenylsulfinyl group, a halo $C_2$–$C_6$ alkenylsulfinyl group, a $C_1$–$C_6$ alkylsulfonyl group, a halo $C_1$–$C_6$ alkylsulfonyl group, a $C_2$–$C_6$ alkenylsulfonyl group, a halo $C_2$–$C_6$ alkenylsulfonyl group, a $C_1$–$C_6$ alkylamino group and a di-$C_1$–$C_6$ alkylamino group;

a naphthyl group; or a substituted naphthyl group having on the ring at least one substituent which may be the same or different and selected from the group consisting of a halogen atom, a cyano group, a nitro group, a $C_1$–$C_6$ alkyl group, a halo $C_1$–$C_6$ alkyl group, a $C_1$–$C_6$ alkoxy group, a halo $C_1$–$C_6$ alkoxy group, a $C_2$–$C_6$ alkenyloxy group, a halo $C_2$–$C_6$ alkenyloxy group, a $C_1$–$C_6$ alkylthio group, a halo $C_1$–$C_6$ alkylthio group, a $C_1$–$C_6$ alkylsulfinyl group, a halo $C_1$–$C_6$ alkylsulfinyl group, a $C_1$–$C_6$ alkylsulfonyl group, a halo $C_1$–$C_6$ alkylsulfonyl group, a $C_2$–$C_6$ alkenylthio group, a halo $C_2$–$C_6$ alkenylthio group, a $C_2$–$C_6$ alkenylsulfinyl group, a halo $C_2$–$C_6$ alkenylsulfinyl group, a $C_2$–$C_6$ alkenylsulfonyl group, a halo $C_2$–$C_6$ alkenylsulfonyl group, a $C_1$–$C_6$ alkylamino group and a di-$C_1$–$C_6$ alkylamino group;

Q represents a group of

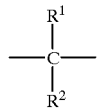

(wherein $R^1$ and $R^2$ may be the same or different and each represent a hydrogen atom, a halogen atom, a $C_1$–$C_6$ alkyl group, a halo $C_1$–$C_6$ alkyl group, a $C_1$–$C_6$ alkoxy group, a halo $C_1$–$C_6$ alkoxy group, a $C_3$–$C_6$ cycloalkyl group or a substituted $C_3$–$C_6$ cycloalkyl group having at least one substituent which may be the same or different and selected from the group consisting of a halogen atom and a $C_1$–$C_6$ alkyl group, and $R^1$ and $R^2$ may be bound to represent a $C_2$–$C_6$ alkylene group which may have on its chain at least one substituent selected from the group consisting of a halogen atom, a $C_1$–$C_6$ alkyl group and a $C_1$–$C_6$ alkoxy group), —CH=CH— or —C≡C—; d is 0 or an integer of 1;

$R^3$ represents a hydrogen atom, a $C_1$–$C_6$ alkyl group, a halo $C_1$–$C_6$ alkyl group, a cyano $C_1$–$C_6$ alkyl group, a $C_1$–$C_6$ alkylthio group, a halo $C_1$–$C_6$ alkylthio group, a $C_2$–$C_6$ alkenyl group or a $C_2$–$C_6$ alkynyl group;

$R^4$, $R^5$, $R^6$, $R^7$ and $R^8$ which may be the same or different and each represents a hydrogen atom, a halogen atom, a $C_1$–$C_6$ alkyl group, a halo $C_1$–$C_6$ alkyl group, a $C_3$–$C_6$ cycloalkyl group or a substituted $C_3$–$C_6$ cycloalkyl group having at least one substituent which may be the same or different and selected from the group consisting of a halogen atom and a $C_1$–$C_6$ alkyl group, a phenyl group or a substituted phenyl group having at least one substituent group which may be the same or different and selected from the group consisting of a halogen atom, a nitro group, a cyano group, a $C_1$–$C_6$ alkyl group, a halo $C_1$–$C_6$ alkyl group, a $C_1$–$C_6$ alkoxy group, a halo $C_1$–$C_6$ alkoxy group, a $C_1$–$C_6$ alkylthio group, a halo $C_1$–$C_6$ alkylthio group, a $C_1$–$C_6$ alkylsulfinyl group, a halo $C_1$–$C_6$ alkylsulfinyl group, a $C_1$–$C_6$ alkylsulfonyl group, a halo $C_1$–$C_6$ alkylsulfonyl group, a $C_1$–$C_6$ alkylamino group and a di-$C_1$–$C_6$ alkylamino group, and $R^4$ and $R^5$ together may form a $C_1$–$C_6$ alkylene group;

W is —O—, —S—, —$SO_2$—, or —N($R^9$)— (wherein $R^9$ represents a hydrogen atom or a $C_1$–$C_6$ alkyl group), and a and b may be the same or different and are 0 or an integer of 1 to 4)).

In the present invention, preferred substituents of the aminoacetonitrile derivative of the formula (I) contain, for example, a phenyl group as the substituent for $Ar^1$ and $Ar^2$, a halogen atom, a halo $C_1$–$C_6$ alkyl group and a halo $C_1$–$C_6$ alkoxy group as the substituent on the ring of $Ar^1$ and $Ar^2$, a hydrogen atom as the substituent for $R^1$, $R^2$, $R^3$, $R^5$ and $R^6$, a $C_1$–$C_6$ alkyl group as the substituent for $R^4$, —$CH_2$— as the substituent for Q, —O— as the substituent for W, and a is preferably an integer of 1 and b is preferably 0.

The aminoacetonitrile derivative of the formula (I) of the present invention contains compounds having stereoisomers and the present invention contains such stereoisomers too.

The aminoacetonitrile derivative of the formula (I) of the present invention can be produced, for example, by the following production method.

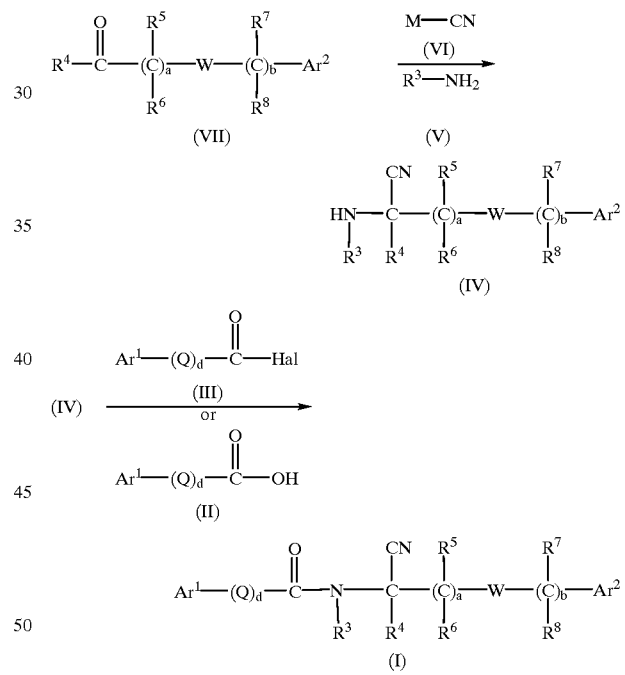

wherein $R^3$, $R^4$, $R^5$, $R^6$, $R^7$, $R^8$, $Ar^1$, $Ar^2$, Q, W, a, b, and d have the same meanings as described above, M represents an alkali metal atom, and Hal represents a halogen atom.)

1. Formula (IV)→Formula (I)

The aminoacetonitrile derivative of the formula (I) can be produced by reacting aminoacetonitrile derivatives of the formula (IV) with acid halides of the formula (III) in the presence of a base (for example, triethylamine, pyridine, etc.). The aminoacetonitrile derivative of the formula (I) can also be produced by condensation-reacting aminoacetonitriles of the formula (IV) with acids of the formula (II) by use of a condensing agent (for example, dicyclohexylcarbodiimide, 2-chloro-1- methylpyridiniumiodide, etc.). The acids of the formula (II) can be produced by known methods (for example, J. Org. Chem. 763, 1948, Organic Synthesis Coll., Vol. 1, 436, J. Org. Chem. 763, 1948, Organic Synthesis Coll., Vol. 1, 336, Beilsteins Handbuch 9, 573, Beilsteins Handbuch 9, 633, etc.).

2. Formula (VII)→Formula (IV)

The aminoacetonitriles of the formula (IV) can be produced, for example, by the reaction of carbonyl compounds of the formula (VII) with metal cyanides of the formula (VI) (for example, sodium cyanide, potassium cyanide, etc.) with amines of the formula (V). As the CN source, organic cyanides such as trimethylsilylnitrile and acetonecyanohydrin can be used. These reactions are a method known as Strecker reaction (for example, Formation of C—C Bonds Vol. 1, Georg Thieme Publishers 1973, Organic Synthesis Coll. Vol., 3, 88, etc.).

The carbonyl compounds of the (VII) can be produced, for example, by the following production method.

The carbonyl compounds of the formula (VII) can be produced, for example, by reacting a compound of the formula (VIII-1) having a leaving group L with a compound of the formula (IX-1) in the presence of a base.

Similarly, the carbonyl compounds of the formula (VII) can also be produced by reacting a compound of the formula (VIII-2) with a compound of the formula (IX-2).

Moreover, the carbonyl compounds of the formula (VII) can be produced by deprotection-reacting a compound of the formula (XII) derived by reacting a compound of the formula (X-1) whose carbonyl group is protected in the form of acetal, ketal or the like with a compound of the formula (IX-1), under acidic conditions. Similarly, the compounds of the formula (XII) can be produced by reacting a compound of the the formula (X-2) with a compound of the formula (IX-2). Further, the carbonyl compounds of the formula (VII) can be produced by oxidizing a compound of the

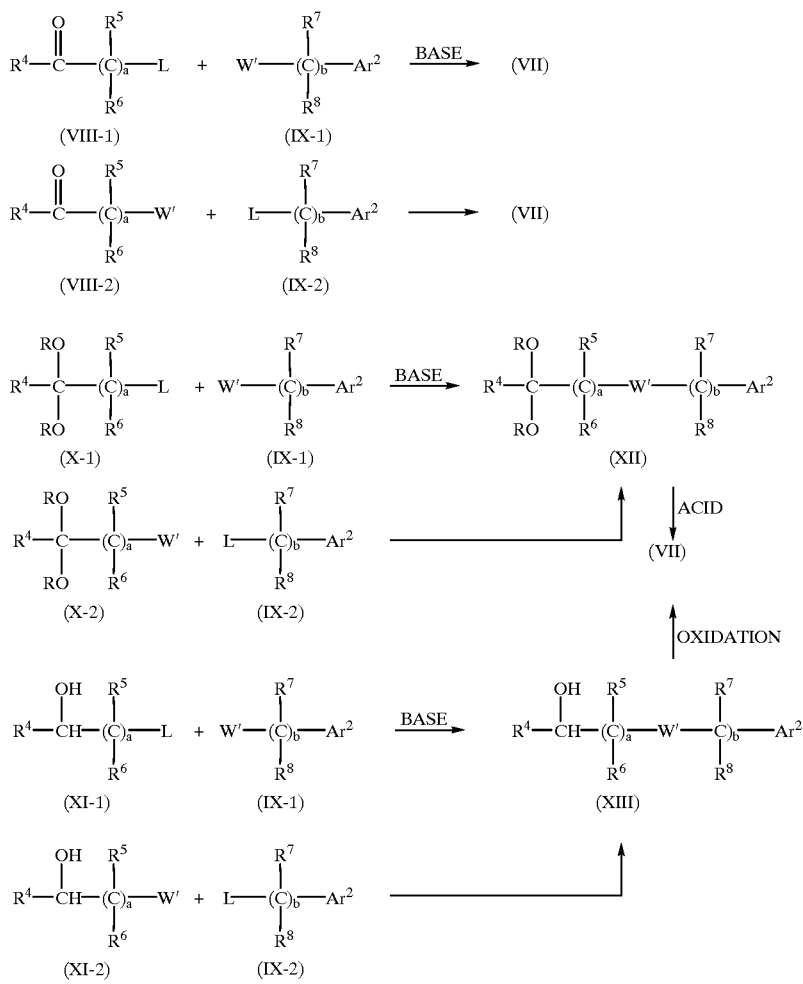

wherein $R^3$, $R^4$, $R^5$, $R^6$, $R^7$, $R^8$, $Ar^1$, $Ar^2$, a and b have the same meanings as described above, L represents a leaving group such as a halogen atom, a methylsulfonyloxy group or a p-methylbenzenesulfonyloxy group, W' is OH, SH or $NHR^9$ (where $R^9$ has the same meaning as described above, Rs are $C_1$–$C_6$ alkyl groups which may be the same or different and represent a $C_1$–$C_4$ alkylene group, or Rs together form a $C_1$14 $C_4$ alkylene group.

formula (XIII) derived by reacting an alcohol compound of the formula (XI-1) with a compound of the formula (IX-1) with using a suitable oxidizing agent (for example, potassium permanganate, etc.). Similarly, the compound of the formula (XIII) can be produced by reacting an alcohol compound of the formula (XI-2) with a compound the formula (IX-2).

Typical compounds of the aminoacetonitrile derivative of the formula (I) of the present invention are shown in Tables 1, 2 and 3.

Formula (I)

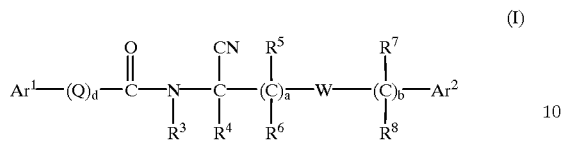

TABLE 1

($R^6=R^7=R^8=H$, $Q=-C(R^1)(R^2)-$, $d=1$, $b=0$ (provided that those described are excepted))

| No. | $Ar^1$ | $Ar^2$ | $R^1$ | $R^2$ | $R^3$ | $R^4$ | $R^5$ | W | a |
|---|---|---|---|---|---|---|---|---|---|
| 1 | Ph | Ph | $(CH_2)_2$ | | H | $CH_3$ | H | O | 1 |
| 2 | Ph | 4-Cl—Ph | H | H | H | $CH_3$ | H | O | 1 |
| 3 | Ph | 4-Cl—Ph | $(CH_2)_2$ | | H | $CH_3$ | H | O | 1 |
| 4 | Ph | 4-$CF_3$—Ph | H | H | H | $CH_3$ | H | O | 1 |
| 5 | Ph | 4-$CHF_2O$—Ph | H | H | W | $CH_3$ | H | O | 1 |
| 6 | Ph | 4-$CF_3O$-Ph | H | H | H | $CH_3$ | H | O | 1 |
| 7 | Ph | 4-$CF_3$S-Ph | H | H | H | $CH_3$ | H | O | 1 |
| 8 | Ph | 4-$CF_3SO_2$—Ph | H | H | H | $CH_3$ | H | O | 1 |
| 9 | Ph | 4-Cl—Ph | $CH_3O$ | H | H | $CH_3$ | H | O | 1 |
| 10 | 2-Cl—Ph | 2-Cl—Ph | H | H | H | $CH_3$ | H | O | 4 |
| 11 | 2-Cl—Ph | 4-Cl—Ph | H | H | H | $CH_3$ | H | O | 2 |
| | | | | | | | | | b = 1 |
| 12 | 2-Cl—Ph | 4-Cl—Ph | H | H | H | H | H | O | 1 |
| 13 | 2-Cl—Ph | 4-Cl—Ph | H | H | H | $CH_3$ | H | O | 1 |
| 14 | 2-Cl—Ph | 4-Cl—Ph | H | H | H | $CH_3$ | $CH_3$ | O | 1 |
| 15 | 2-Cl—Ph | 4-Cl—Ph | H | H | H | $CH_3$ | $CH_3$ | O | 1 |
| 16 | 2-Cl—Ph | 4-Cl—Ph | H | H | H | $CH_3$ | n-$C_3H_7$ | O | 1 |
| 17 | 2-Cl—Ph | 4-Cl—Ph | H | H | H | $CH_3$ | n-$C_3H_7$ | O | 1 |
| 18 | 2-Cl—Ph | 4-Cl—Ph | H | H | H | $CH_3$ | n-$C_4H_9$ | O | 1 |
| 19 | 2-Cl—Ph | 4-Cl—Ph | H | H | H | $CH_3$ | n-$C_4H_9$ | O | 1 |
| 20 | 2-Cl—Ph | 4-Cl—Ph | H | H | H | $CH_3$ | H | O | 4 |
| 21 | 2-Cl—Ph | 4-Cl—Ph | H | H | H | $C_2H_5$ | H | O | 1 |
| 22 | 2-Cl—Ph | 4-Cl—Ph | H | H | H | n-$C_3H_7$ | H | O | 1 |
| 23 | 2-Cl—Ph | 4-Cl—Ph | H | H | H | i-$C_3H_7$ | H | O | 1 |
| 24 | 2-Cl—Ph | 4-Cl—Ph | H | H | H | c-$C_3H_5$ | H | O | 1 |
| 25 | 2-Cl—Ph | 4-Cl—Ph | H | H | H | t-$C_4H_9$ | H | O | 1 |
| 26 | 2-Cl—Ph | 4-Cl—Ph | H | H | H | $(CH_2)_4$ | | O | 1 |
| 27 | 2-Cl—Ph | 4-Cl—Ph | H | H | $CH_3$ | $CH_3$ | H | O | 1 |
| 28 | 2-Cl—Ph | 4-Cl—Ph | H | H | $C_2H_5$ | $CH_3$ | H | O | 1 |
| 29 | 2-Cl—Ph | 4-Cl—Ph | H | H | n-$C_4H_9$ | $CH_3$ | H | O | 1 |
| 30 | 2-Cl—Ph | 4-Cl—Ph | H | H | $CH_2C\equiv CH$ | $CH_3$ | H | O | 1 |
| 31 | 2-Cl—Ph | 4-$CF_3$—Ph | H | H | H | $CH_3$ | H | O | 1 |
| 32 | 2-Cl—Ph | 4-$CF_3$—Ph | H | H | H | $CH_3$ | H | O | 1 |
| 33 | 2-Cl—Ph | 4-$CF_3O$—Ph | H | H | H | $CH_3$ | H | O | 1 |
| 34 | 2-Cl—Ph | 4-$CHF_2O$—Ph | H | H | H | $CH_3$ | H | O | 1 |
| 35 | 2-Cl—Ph | 4-$CF_3S$—Ph | H | H | H | $CH_3$ | H | O | 1 |
| 36 | 2-Cl—Ph | 4-$CF_3SO_2$—Ph | H | H | H | $CH_3$ | H | O | 1 |
| 37 | 2-F—Ph | 4-$CF_3O$—Ph | H | H | H | $CH_3$ | H | O | 1 |
| 38 | 2-F—Ph | 4-$CHF_2O$—Ph | H | H | H | $CH_3$ | H | O | 1 |
| 39 | 2-F—Ph | 4-$CF_3S$—Ph | H | H | H | $CH_3$ | H | O | 1 |
| 40 | 2-F—Ph | 4-$CF_3SO_2$—Ph | H | H | H | $CH_3$ | H | O | 1 |
| 41 | 2-F—Ph | 4-Cl—Ph | H | H | H | $CH_3$ | H | O | 1 |
| 42 | 2-F—Ph | 4-Cl—Ph | $(CH_2)_2$ | | H | $CH_3$ | H | O | 1 |
| 43 | 2-F—Ph | 4-$CF_3$—Ph | H | H | H | $CH_3$ | H | O | 1 |
| 44 | 3-Cl—Ph | 4-Cl—Ph | H | H | H | $CH_3$ | $CH_3$ | O | 1 |
| 45 | 3-Cl—Ph | 4-Cl—Ph | H | H | H | $CH_3$ | $CH_3$ | O | 1 |
| 46 | 3-Cl—Ph | 4-Cl—Ph | H | H | H | $CH_3$ | n-$C_3H_7$ | O | 1 |
| 47 | 3-Cl—Ph | 4-Cl—Ph | H | H | H | $CH_3$ | n-$C_3H_7$ | O | 1 |
| 48 | 3-Cl—Ph | 4-Cl—Ph | H | H | H | $C_2H_5$ | H | O | 1 |
| 49 | 3-Cl—Ph | 4-Cl—Ph | H | H | H | $CH_3$ | H | O | 1 |
| 50 | 3-Cl—Ph | 4-Cl—Ph | H | H | H | $CH_3$ | H | O | 4 |
| 51 | 3-Cl—Ph | 4-Cl—Ph | H | H | H | n-$C_3H_7$ | H | O | 1 |
| 52 | 3-Cl—Ph | 4-Cl—Ph | H | H | H | i-$C_3H_7$ | H | O | 1 |
| 53 | 3-Cl—Ph | 4-Cl—Ph | H | H | H | c-$C_3H_5$ | H | O | 1 |
| 54 | 3-Cl—Ph | 4-Cl—Ph | H | H | H | t-$C_4H_9$ | H | O | 1 |
| 55 | 3-Cl—Ph | 4-Cl—Ph | H | H | H | $(CH_2)_4$ | | O | 1 |

TABLE 1-continued $(R^6=R^7=R^8=H, Q=-C(R^1)(R^2)-, d=1, b=0$ (provided that those described are excepted)

| No. | Ar$^1$ | Ar$^2$ | R$^1$ | R$^2$ | R$^3$ | R$^4$ | R$^5$ | W | a |
|---|---|---|---|---|---|---|---|---|---|
| 56 | 3-Cl—Ph | 4-Cl—Ph | (CH$_2$)$_2$ | | H | CH$_3$ | H | O | 1 |
| 57 | 4-Cl—Ph | Ph | H | H | H | CH$_3$ | H | O | 1 |
| 58 | 4-Cl—Ph | Ph | H | H | H | CH$_3$ | H | S | 1 |
| 59 | 4-Cl—Ph | Ph | H | H | H | CH$_3$ | H | SO$_2$ | 1 |
| 60 | 4-Cl—Ph | 2-Cl—Ph | H | H | H | CH$_3$ | H | O | 1 |
| 61 | 4-Cl—Ph | 2-Cl—Ph | H | H | H | CH$_3$ | H | O | 4 |
| 62 | 4-Cl—Ph | 3-Cl—Ph | H | H | H | CH$_3$ | H | O | 1 |
| 63 | 4-Cl—Ph | 4-Cl—Ph | H | H | H | H | H | O | 1 |
| 64 | 4-Cl—Ph | 4-Cl—Ph | H | H | H | CH$_3$ | H | O | 1 |
| 65 | 4-Cl—Ph | 4-Cl—Ph | H | H | H | CH$_3$ | H | O | 2 |
| | | | | | | | | | b = 1 |
| 66 | 4-Cl—Ph | 4-Cl—Ph | H | H | H | CH$_3$ | H | S | 1 |
| 67 | 4-Cl—Ph | 4-Cl—Ph | H | H | H | CH$_3$ | H | SO$_2$ | 1 |
| 68 | 4-Cl—Ph | 4-Cl—Ph | H | H | H | CH$_3$ | H | O | 4 |
| 69 | 4-Cl—Ph | 4-Cl—Ph | H | H | H | CH$_3$ | CH$_3$ | O | 1 |
| 70 | 4-Cl—Ph | 4-Cl—Ph | H | H | H | CH$_3$ | n-C$_3$H$_7$ | O | 1 |
| 71 | 4-Cl—Ph | 4-Cl—Ph | H | H | H | CH$_3$ | n-C$_4$H$_9$ | O | 1 |
| 72 | 4-Cl—Ph | 4-Cl—Ph | H | H | H | CH$_3$ | CF$_3$ | O | 1 |
| 73 | 4-Cl—Ph | 4-Cl—Ph | H | H | H | C$_2$H$_5$ | H | O | 1 |
| 74 | 4-Cl—Ph | 4-Cl—Ph | H | H | H | n-C$_3$H$_7$ | H | O | 1 |
| 75 | 4-Cl—Ph | 4-Cl—Ph | H | H | H | i-C$_3$H$_7$ | H | O | 1 |
| 76 | 4-Cl—Ph | 4-Cl—Ph | H | H | H | c-C$_3$H$_5$ | H | O | 1 |
| 77 | 4-Cl—Ph | 4-Cl—Ph | H | H | H | t-C$_4$H$_9$ | H | O | 1 |
| 78 | 4-Cl—Ph | 4-Cl—Ph | H | H | H | CF$_3$ | H | O | 1 |
| 79 | 4-Cl—Ph | 4-Cl—Ph | H | H | H | (CH$_2$)$_4$ | | O | 1 |
| 80 | 4-Cl—Ph | 4-Cl—Ph | H | H | CH$_3$ | CH$_3$ | H | O | 1 |
| 81 | 4-Cl—Ph | 4-Cl—Ph | H | H | C$_2$H$_5$ | CH$_3$ | H | O | 1 |
| 82 | 4-Cl—Ph | 4-Cl—Ph | H | H | n-C$_4$H$_9$ | CH$_3$ | H | O | 1 |
| 83 | 4-Cl—Ph | 4-Cl—Ph | H | H | CH$_2$C≡CH | CH$_3$ | H | O | 1 |
| 84 | 4-Cl—Ph | 4-Cl—Ph | CH$_3$ | CH$_3$ | H | CH$_3$ | H | O | 1 |
| 85 | 4-Cl—Ph | 4-Cl—Ph | i-C$_3$H$_7$ | H | H | CH$_3$ | H | O | 1 |
| 86 | 4-Cl—Ph | 4-Cl—Ph | i-C$_3$H$_7$ | H | H | CH$_3$ | H | O | 1 |
| 87 | 4-Cl—Ph | 4-Cl—Ph | CF$_3$ | H | H | CH$_3$ | H | O | 1 |
| 88 | 4-Cl—Ph | 4-Cl—Ph | (CH$_2$)$_2$ | | H | CH$_3$ | H | O | 1 |
| 89 | 4-Cl—Ph | 4-Cl—Ph | (CH$_2$) | | H | CH$_3$ | H | O | 1 |
| 90 | 4-Cl—Ph | 4-Cl—Ph | (CH$_2$)$_4$ | | H | CH$_3$ | H | O | 1 |
| 91 | 4-Cl—Ph | 4-Cl—Ph | F | F | H | CH$_3$ | H | O | 1 |
| 92 | 4-Cl—Ph | 4-I-Ph | H | H | H | CH$_3$ | H | O | 1 |
| 93 | 4-Cl—Ph | 4-Br-Ph | H | H | H | CH$_3$ | H | O | 1 |
| 94 | 4-Cl—Ph | 4-F—Ph | H | H | H | CH$_3$ | H | O | 1 |
| 95 | 4-Cl—Ph | 3-CF$_3$—Ph | H | H | H | CH$_3$ | H | O | 1 |
| 96 | 4-Cl—Ph | 4-CF$_3$—Ph | H | H | H | CH$_3$ | H | O | 1 |
| 97 | 4-Cl—Ph | 4-C$_2$F$_5$—Ph | H | H | H | CH$_3$ | H | O | 1 |
| 98 | 4-Cl—Ph | 4-i-C$_3$F$_7$—Ph | H | H | H | CH$_3$ | H | O | 1 |
| 99 | 4-Cl—Ph | 4-CF$_3$—Ph | (CH$_2$)$_2$ | | H | CH$_3$ | H | O | 1 |
| 100 | 4-Cl—Ph | 4-n-C$_3$F$_7$—Ph | H | H | H | CH$_3$ | H | O | 1 |
| 101 | 4-Cl—Ph | 4-CH$_3$—Ph | H | H | H | CH$_3$ | H | O | 1 |
| 102 | 4-Cl—Ph | 4-t-C$_4$H$_9$—Ph | H | H | H | CH$_3$ | H | O | 1 |
| 103 | 4-Cl—Ph | 4-(t-C$_4$H$_9$—C≡C)—Ph | H | H | H | CH$_3$ | H | O | 1 |
| 104 | 4-Cl—Ph | 4-CH$_3$O—Ph | H | H | H | CH$_3$ | H | O | 1 |
| 105 | 4-Cl—Ph | 4-CF$_3$O—Ph | H | H | H | CH$_3$ | H | O | 1 |
| 106 | 4-Cl—Ph | 4-CHF$_2$O—Ph | H | H | H | CH$_3$ | H | O | 1 |
| 107 | 4-Cl—Ph | 4-CF$_3$SO$_2$—Ph | H | H | H | CH$_3$ | H | O | 1 |
| 108 | 4-Cl—Ph | 4-CH$_3$S—Ph | H | H | H | CH$_3$ | H | O | 1 |
| 109 | 4-Cl—Ph | 4-CH$_3$SO$_2$—Ph | H | H | H | CH$_3$ | H | O | 1 |
| 110 | 4-Cl—Ph | 4-CF$_3$S—Ph | H | H | H | CH$_3$ | H | O | 1 |
| 111 | 4-Cl—Ph | 4-CF$_3$SO$_2$—Ph | H | H | H | CH$_3$ | H | O | 1 |
| 112 | 4-Cl—Ph | 4-CHF$_2$S—Ph | H | H | H | CH$_3$ | H | O | 1 |
| 113 | 4-Cl—Ph | 4-CHF$_2$SO$_2$—Ph | H | H | H | CF$_3$ | H | O | 1 |
| 114 | 4-Cl—Ph | 4-n-C$_3$F$_7$S—Ph | H | H | H | CH$_3$ | H | O | 1 |
| 115 | 4-Cl—Ph | 4-i-C$_3$F$_7$S—Ph | H | H | H | CH$_3$ | H | O | 1 |
| 116 | 4-Cl—Ph | 4-n-C$_3$F$_7$SO$_2$—Ph | H | H | H | CH$_3$ | H | O | 1 |
| 117 | 4-Cl—Ph | 4-n-C$_6$F$_{13}$S—Ph | H | H | H | CH$_3$ | H | O | 1 |
| 118 | 4-Cl—Ph | 4-n-C$_6$F$_{13}$SO$_2$—Ph | H | H | H | CH$_3$ | H | O | 1 |
| 119 | 4-Cl—Ph | 4-CF$_3$SO$_2$NH—Ph | H | H | H | CH$_3$ | H | O | 1 |
| 120 | 4-Cl—Ph | 4-(5-CF$_3$-2-Pyr)O—Ph | H | H | H | CH$_3$ | H | O | 1 |
| 121 | 4-Cl—Ph | 2,4-Cl$_2$—Ph | H | H | H | CH$_3$ | H | O | 1 |
| 122 | 4-Cl—Ph | 3,4-Cl$_2$—Ph | H | H | H | CH$_3$ | H | O | 1 |
| 123 | 4-Cl—Ph | 3-Cl-4-F—Ph | H | H | H | CH$_3$ | H | O | 1 |
| 124 | 4-Cl—Ph | 3-CF$_3$—4-NO$_2$—Ph | H | H | H | CH$_3$ | H | O | 1 |
| 125 | 4-Cl—Ph | 3,5-(CH$_3$)$_2$-Ph | H | H | H | CH$_3$ | H | O | 1 |
| 126 | 4-Cl—Ph | 2,3,4,5,6-F$_6$—Ph | H | H | H | CH$_3$ | H | O | 1 |

TABLE 1-continued ($R^6$=$R^7$=$R^8$=H, Q=—C($R^1$)($R^2$)—, d=1, b=0 (provided that those described are excepted)

| No. | $Ar^1$ | $Ar^2$ | $R^1$ | $R^2$ | $R^3$ | $R^4$ | $R^5$ | W | a |
|---|---|---|---|---|---|---|---|---|---|
| 127 | 4-Cl—Ph | 4-(Cl$_2$C=CH—CH$_2$O)—Ph | H | H | H | CH$_3$ | H | O | 1 |
| 128 | 4-Cl—Ph | 4-(Cl$_2$C=CH—CH$_2$S)—Ph | H | H | H | CH$_3$ | H | O | 1 |
| 129 | 4-Cl—Ph | 4-(Cl$_2$C=CH—CH$_2$SO$_2$)—Ph | H | H | H | CH$_3$ | H | O | 1 |
| 130 | 4-Cl—Ph | 2,6-Cl$_2$-4-(Cl$_2$—C=CHCH$_2$O)—Ph | H | H | H | CH$_3$ | H | O | 1 |
| 131 | 4-Cl—Ph | 4-CN—Ph | H | H | H | CH$_3$ | H | O | 1 |
| 132 | 4-Cl—Ph | 4-NO$_2$-Ph | H | H | H | CH$_3$ | H | O | 1 |
| 133 | 4-Cl—Ph | 4-(Ph—C≡C)Ph | H | H | H | CH$_3$ | H | O | 1 |
| 134 | 4-Cl—Ph | 2-Naph | H | H | H | CH$_3$ | H | O | 1 |
| 135 | 4-Cl—Ph | 6-Cl-2-Naph | H | H | H | CH$_3$ | H | O | 1 |
| 136 | 4-Cl—Ph | 6-CF$_3$-2-Naph | H | H | H | CH$_3$ | H | O | 1 |
| 137 | 4-Cl—Ph | 5-Cl-2-Pyr | H | H | H | CH$_3$ | H | O | 1 |
| 138 | 4-Cl—Ph | 6-Cl-3-Pyr | H | H | H | CH$_3$ | H | O | 1 |
| 139 | 4-Cl—Ph | 5-NO$_2$-2-Pyr | H | H | H | CH$_3$ | H | O | 1 |
| 140 | 4-Cl—Ph | 5-CN-2-Pyr | H | H | H | CH$_3$ | H | O | 1 |
| 141 | 4-F—Ph | 4-Cl—Ph | H | H | H | CH$_3$ | H | O | 1 |
| 142 | 4-F—Ph | 4-Cl—Ph | H | H | H | CH$_3$ | H | N—CH$_3$ | 1 |
| 143 | 4-F—Ph | 4-F—Ph | H | H | H | CH$_3$ | H | O | 1 |
| 144 | 4-F—Ph | 4-I—Ph | H | H | H | CH$_3$ | H | O | 1 |
| 145 | 4-F—Ph | 4-i-C$_3$H$_7$—Ph | H | H | H | CH$_3$ | H | O | 1 |
| 146 | 4-F—Ph | 4-CF$_3$O—Ph | H | H | H | CH$_3$ | H | O | 1 |
| 147 | 4-F—Ph | 4-CF$_3$—Ph | H | H | H | CH$_3$ | H | O | 1 |
| 148 | 4-F—Ph | 4-CN—Ph | H | H | H | CH$_3$ | H | O | 1 |
| 149 | 4-F—Ph | 4-NO$_2$-Ph | H | H | H | CH$_3$ | H | O | 1 |
| 150 | 4-F—Ph | 3-Cl-4-F—Ph | H | H | H | CH$_3$ | H | O | 1 |
| 151 | 4-F—Ph | 2,3,4,5,6-F$_5$—Ph | H | H | H | CH$_3$ | H | O | 1 |
| 152 | 4-F—Ph | 6-Cl-2-Pyr | H | H | H | CH$_3$ | H | O | 1 |
| 153 | 4-Br—Ph | 4-Cl—Ph | H | H | H | CH$_3$ | H | O | 1 |
| 154 | 2-I—Ph | 4-CF$_3$—Ph | H | H | H | CH$_3$ | H | O | 1 |
| 155 | 4-I—Ph | 4-Cl—Ph | H | H | H | CH$_3$ | H | O | 1 |
| 156 | 4-I—Ph | 4-I—Ph | H | H | H | CH$_3$ | H | O | 1 |
| 157 | 4-I—Ph | 4-CF$_3$—Ph | H | H | H | CH$_3$ | H | O | 1 |
| 158 | 2-CH$_3$—Ph | 3,5-(CH$_3$)$_2$-Ph | H | H | H | CH$_3$ | H | O | 1 |
| 159 | 2-CH$_3$—Ph | 4-CF$_3$—Ph | H | H | H | CH$_3$ | H | O | 1 |
| 160 | 3-CH$_3$—Ph | 3,5-(CH$_3$)$_2$-Ph | H | H | H | CH$_3$ | H | O | 1 |
| 161 | 4-CH$_3$—Ph | 3,5-(CH$_3$)$_2$-Ph | H | H | H | CH$_3$ | H | O | 1 |
| 162 | 2-CH$_3$O—Ph | 3,5-(CH$_3$)$_2$-Ph | H | H | H | CH$_3$ | H | O | 1 |
| 163 | 3-CF$_3$—Ph | 4-Cl—Ph | H | H | H | CH$_3$ | H | O | 1 |
| 164 | 4-CH$_3$O—Ph | 3,5-(CH$_3$)$_2$ | H | H | H | CH$_3$ | H | O | 1 |
| 165 | 4-CH$_3$O—Ph | 4-Cl—Ph | H | H | H | CH$_3$ | H | O | 1 |
| 166 | 4-CH$_3$O—Ph | 4-Cl—Ph | H | H | H | CH$_3$ | CH$_3$ | O | 1 |
| 167 | 4-CH$_3$O—Ph | 4-Cl—Ph | H | H | H | CH$_3$ | n-C$_3$H$_7$ | O | 1 |
| 168 | 4-CH$_3$O—Ph | 4-Cl—Ph | H | H | H | CH$_3$ | n-C$_3$H$_7$ | O | 1 |
| 169 | 4-CH$_3$O—Ph | 4-Cl—Ph | H | H | H | CH$_3$ | n-C$_4$H$_9$ | O | 1 |
| 170 | 4-CH$_3$O—Ph | 4-Cl—Ph | H | H | H | CH$_3$ | H | O | 4 |
| 171 | 4-CH$_3$O—Ph | 4-Cl—Ph | H | H | H | C$_2$H$_5$ | H | O | 1 |
| 172 | 4-CH$_3$O—Ph | 4-Cl—Ph | H | H | H | n-C$_3$H$_7$ | H | O | 1 |
| 173 | 4-CH$_3$O—Ph | 4-Cl—Ph | H | H | H | i-C$_3$H$_7$ | H | O | 1 |
| 174 | 4-CH$_3$O—Ph | 4-Cl—Ph | H | H | H | c-C$_3$H$_5$ | H | O | 1 |
| 175 | 4-CH$_3$O—Ph | 4-Cl—Ph | H | H | H | t-C$_4$H$_9$ | H | O | 1 |
| 176 | 4-CH$_3$O—Ph | 4-Cl—Ph | H | H | H | (CH$_2$)$_4$ | | O | 1 |
| 177 | 4-CF$_3$O—Ph | 4-Cl—Ph | H | H | H | CH$_3$ | H | O | 1 |
| 178 | 4-CHF$_2$O—Ph | 4-Cl—Ph | H | H | H | CH$_3$ | H | O | 1 |
| 179 | 4-CF$_3$SO$_2$O—Ph | 4-Cl—Ph | H | H | H | CH$_3$ | H | O | 1 |
| 180 | 4-CHF$_2$S—Ph | 4-Cl—Ph | H | H | H | CH$_3$ | H | O | 1 |
| 181 | 4-CHF$_2$SO$_2$—Ph | 4-Cl—Ph | H | H | H | CH$_3$ | H | O | 1 |
| 182 | 4-CF$_3$S—Ph | 4-Cl—Ph | H | H | H | CH$_3$ | H | O | 1 |
| 183 | 4-CF$_3$SO$_2$—Ph | 4-Cl—Ph | H | H | H | CH$_3$ | H | O | 1 |
| 184 | 4-n-C$_3$F$_7$—Ph | 4-Cl—Ph | H | H | H | CH$_3$ | H | O | 1 |
| 185 | 4-CF$_3$SO$_2$NH—Ph | 4-Cl—Ph | H | H | H | CH$_3$ | H | O | 1 |
| 186 | 4-CF$_3$—Ph | 2-Cl—Ph | H | H | H | CH$_3$ | H | O | 1 |
| 187 | 4-CF$_3$—Ph | 4-Cl—Ph | H | H | H | CH$_3$ | H | O | 1 |
| 188 | 4-CF$_3$—Ph | 4-F—Ph | H | H | H | CH$_3$ | H | O | 1 |
| 189 | 4-CF$_3$—Ph | 4-I—Ph | H | H | H | CH$_3$ | H | O | 1 |

TABLE 1-continued ($R^6$=$R^7$=$R^8$=H, Q=—C($R^1$)($R^2$)—, d=1, b=0 (provided that those described are excepted)

| No. | $Ar^1$ | $Ar^2$ | $R^1$ | $R^2$ | $R^3$ | $R^4$ | $R^5$ | W | a |
|---|---|---|---|---|---|---|---|---|---|
| 190 | 4-$CF_3$—Ph | 2,4-$Cl_2$—Ph | H | H | H | $CH_3$ | H | O | 1 |
| 191 | 4-$CF_3$—Ph | 2,4-$F_2$—Ph | H | H | H | $CH_3$ | H | O | 1 |
| 192 | 4-$CF_3$—Ph | 2,6-$F_2$—Ph | H | H | H | $CH_3$ | H | O | 1 |
| 193 | 4-$CF_3$—Ph | 4-I-2-$CH_3$—Ph | H | H | H | $CH_3$ | H | O | 1 |
| 194 | 4-$CF_3$—Ph | 4-$CH_3$—Ph | H | H | H | $CH_3$ | H | O | 1 |
| 195 | 4-$CF_3$—Ph | 4-$CF_3$—Ph | H | H | H | $CH_3$ | H | O | 1 |
| 196 | 4-$CF_3$—Ph | 4-$C_2F_3$—Ph | H | H | H | $CH_3$ | H | O | 1 |
| 197 | 4-$CF_3$—Ph | 4-n-$C_3F_7$—Ph | H | H | H | $CH_3$ | H | O | 1 |
| 198 | 4-$CF_3$—Ph | 4-i-$C_3F_7$—Ph | H | H | H | $CH_3$ | H | O | 1 |
| 199 | 4-$CF_3$—Ph | 4-(PhO)—Ph | H | H | H | $CH_3$ | H | O | 1 |
| 200 | 4-$CF_3$—Ph | 4-$CF_3$O—Ph | H | H | H | $CH_3$ | H | O | 1 |
| 201 | 4-$CF_3$—Ph | 4-$CHF_2$O—Ph | H | H | H | $CH_3$ | H | O | 1 |
| 202 | 4-$CF_3$—Ph | 4-$CF_3SO_2$O—Ph | H | H | H | $CH_3$ | H | O | 1 |
| 203 | 4-$CF_3$—Ph | 4-$CF_3$S—Ph | H | H | H | $CH_3$ | H | O | 1 |
| 204 | 4-$CF_3$—Ph | 4-$CF_3SO_2$—Ph | H | H | H | $CH_3$ | H | O | 1 |
| 205 | 4-$CF_3$—Ph | 4-$CHF_2$S—Ph | H | H | H | $CH_3$ | H | O | 1 |
| 206 | 4-$CF_3$—Ph | 4-$CHF_2SO_2$—Ph | H | H | H | $CH_3$ | H | O | 1 |
| 207 | 4-$CF_3$—Ph | 4-n-$C_3F_7$S—Ph | H | H | H | $CH_3$ | H | O | 1 |
| 208 | 4-$CF_3$—Ph | 4-i-$C_3F_7$S—Ph | H | H | H | $CH_3$ | H | O | 1 |
| 209 | 4-$CF_3$—Ph | 4-n-$C_3F_7SO_2$—Ph | H | H | H | $CH_3$ | H | O | 1 |
| 210 | 4-$CF_3$—Ph | 4-n-$C_6F_{13}$S—Ph | H | H | H | $CH_3$ | H | O | 1 |
| 211 | 4-$CF_3$—Ph | 4-n-$C_6F_{13}SO_2$-Ph | H | H | H | $CH_3$ | H | O | 1 |
| 212 | 4-$CF_3$—Ph | 4-$CF_3SO_2$NH—Ph | H | H | H | $CH_3$ | H | O | 1 |
| 213 | 4-$CF_3$—Ph | 4-$COOCH_3$—Ph | H | H | H | $CH_3$ | H | O | 1 |
| 214 | 4-$CF_3$—Ph | 2-($Cl_2$C=CH—$CH_2$O)—Ph | H | H | H | $CH_3$ | H | O | 1 |
| 215 | 4-$CF_3$—Ph | 4-($Cl_2$C=CH—$CH_2$S)—Ph | H | H | H | $CH_3$ | H | O | 1 |
| 216 | 4-$CF_3$—Ph | 4-($Cl_2$C=CH—$CH_2SO_2$)—Ph | H | H | H | $CH_3$ | H | O | 1 |
| 217 | 4-$CF_3$—Ph | 2,6-$Cl_2$-4-($Cl_2$-C=CH$CH_2$O)—Ph | H | H | H | $CH_3$ | H | O | 1 |
| 218 | 4-$CF_3$—Ph—Ph | 4-(t-$C_4H_9$C≡C) | H | H | H | $CH_3$ | H | O | 1 |
| 219 | 4-$CF_3$—Ph—Ph | 4-(Ph—C≡C) | H | H | H | $CH_3$ | H | O | 1 |
| 220 | 4-$C_2F_5$—Ph | 4-Cl—Ph | H | H | H | $CH_3$ | H | O | 1 |
| 221 | 4-$C_2F_5$—Ph | 4-$CF_3$—Ph | H | H | H | $CH_3$ | H | O | 1 |
| 222 | 4-$C_2F_5$—Ph | 4-i-$C_3F_7$—Ph | H | H | H | $CH_3$ | H | O | 1 |
| 223 | 4-n-$C_3F_7$—Ph | 4-Cl—Ph | H | H | H | $CH_3$ | H | O | 1 |
| 224 | 4-n-$C_3F_7$—Ph | 4-$CF_3$—Ph | H | H | H | $CH_3$ | H | O | 1 |
| 225 | 4-n-$C_3F_7$—Ph | 4-i-$C_3F_7$—Ph | H | H | H | $CH_3$ | H | O | 1 |
| 226 | 4-i-$C_3F_7$—Ph | 4-Cl—Ph | H | H | H | $CH_3$ | H | O | 1 |
| 227 | 4-i-$C_3F_7$—Ph | 4-$CF_3$—Ph | H | H | H | $CH_3$ | H | O | 1 |
| 228 | 4-i-$C_3F_7$—Ph | 4-i-$C_3F_7$—Ph | H | H | H | $CH_3$ | H | O | 1 |
| 229 | 4-$NO_2$—Ph | 4-F—Ph | H | H | H | $CH_3$ | H | O | 1 |
| 230 | 4-Ph—Ph | 4-Cl—Ph | H | H | H | $CH_3$ | H | O | 1 |
| 231 | 2,4-$Cl_2$—Ph | 4-Cl—Ph | H | H | H | $CH_3$ | H | O | 1 |
| 232 | 2,4-$Cl_2$—Ph | 4-Cl—Ph | $CH_3$O | H | H | $CH_3$ | H | O | 1 |
| 233 | 2,4-$Cl_2$—Ph | 4-$CF_3$—Ph | H | H | H | $CH_3$ | H | O | 1 |
| 234 | 2,6-$Cl_2$—Ph | 4-Cl—Ph | H | H | H | $CH_3$ | H | O | 1 |
| 235 | 2,6-$F_2$—Ph | 4-Cl—Ph | H | H | H | $CH_3$ | H | O | 1 |
| 236 | 2,6-$F_2$—Ph | 4-$CF_3$—Ph | H | H | H | $CH_3$ | H | O | 1 |
| 237 | 3,4-$F_2$—Ph | 4-F—Ph | H | H | H | $CH_3$ | H | O | 1 |
| 238 | 3,4-$F_2$—Ph | 4-$CF_3$—Ph | H | H | H | $CH_3$ | H | O | 1 |
| 239 | 2,3-($CH_3$)$_2$-Ph | 3,5-($CH_3$)$_2$-Ph | H | H | H | $CH_3$ | H | O | 1 |
| 240 | 3,5-($CH_3$)$_2$-Ph | 4-$CH_3$—Ph | H | H | H | $CH_3$ | H | O | 1 |
| 241 | 3,5-($CH_3$)$_2$-Ph | 4-$OCH_3$—Ph | H | H | H | $CH_3$ | H | O | 1 |
| 242 | 3,5-($CH_3$)$_2$-Ph | 2,3-($CH_3$)$_2$-Ph | H | H | H | $CH_3$ | H | O | 1 |
| 243 | 3,5-($CF_3$)$_2$-Ph | 4-$CF_3$—Ph | H | H | H | $CH_3$ | H | O | 1 |
| 244 | 2,4,6-($CH_3$)$_3$-Ph | 4-Cl—Ph | H | H | H | $CH_3$ | H | O | 1 |
| 245 | 2,3,4,5,6-$F_5$—Ph | 4-F—Ph | H | H | H | $CH_3$ | H | O | 1 |
| 246 | 5-Cl-2-Pyr | 4-Cl—Ph | H | H | H | $CH_3$ | H | O | 1 |
| 247 | 5-Cl-2-Pyr | 4-$CF_3$—Ph | H | H | H | $CH_3$ | H | O | 1 |
| 248 | 5-Cl-2-Pyr | 5-Cl-2-Pyr | H | H | H | $CH_3$ | H | O | 1 |
| 249 | 5-Cl-2-Pyr | 5-$CF_3$-2-Pyr | H | H | H | $CH_3$ | H | O | 1 |
| 250 | 6-Cl-3-Pyr | 4-Cl—Ph | H | H | H | $CH_3$ | H | O | 1 |
| 251 | 6-Cl-3-Pyr | 4-$CF_3$—Ph | H | H | H | $CH_3$ | H | O | 1 |
| 252 | 5-$CF_3$-2-Pyr | 4-Cl—Ph | H | H | H | $CH_3$ | H | O | 1 |
| 253 | 5-$CF_3$-2-Pyr | 4-$CF_3$—Ph | H | H | H | $CH_3$ | H | O | 1 |

TABLE 1-continued ($R^6=R^7=R^8=H$, $Q=-C(R^1)(R^2)-$, $d=1$, $b=0$ (provided that those described are excepted))

| No. | $Ar^1$ | $Ar^2$ | $R^1$ | $R^2$ | $R^3$ | $R^4$ | $R^5$ | W | a |
|---|---|---|---|---|---|---|---|---|---|
| 254 | 5-CF$_3$-2-Pyr | 4-Cl-2-Pyr | H | H | H | CH$_3$ | H | O | 1 |
| 255 | 5-CF$_3$-2-Pyr | 4-CF$_3$-2-Pyr | H | H | H | CH$_3$ | H | O | 1 |
| 256 | 6-CF$_3$-3-Pyr | 4-Cl—Ph | H | H | H | CH$_3$ | H | O | 1 |
| 257 | 6-CF$_3$-3-Pyr | 4-CF$_3$—Ph | H | H | H | CH$_3$ | H | O | 1 |
| 258 | 5-CN-2-Pyr | 4-Cl—Ph | H | H | H | CH$_3$ | H | O | 1 |
| 259 | 5-NO$_2$-2-Pyr | 4-Cl—Ph | H | H | H | CH$_3$ | H | O | 1 |
| 260 | 5-CF$_3$O-2-Pyr | 4-Cl—Ph | H | H | H | CH$_3$ | H | O | 1 |
| 261 | 5-CF$_3$O-2-Pyr | 4-CF$_3$—Ph | H | H | H | CH$_3$ | H | O | 1 |
| 262 | 5-CF$_3$S-2-Pyr | 4-Cl—Ph | H | H | H | CH$_3$ | H | O | 1 |
| 263 | 5-CF$_3$S-2-Pyr | 4-CF$_3$—Ph | H | H | H | CH$_3$ | H | G | 1 |
| 264 | 5-CF$_3$SO$_2$-2-Pyr | 4-Cl—Ph | H | H | H | CH$_3$ | H | O | 1 |
| 265 | 5-CF$_3$SO$_2$-2-Pyr | 4-CF$_3$—Ph | H | H | H | CH$_3$ | H | O | 1 |
| 266 | 3,5-Cl$_2$-2-Pyr | 4-Cl—Ph | H | H | H | CH$_3$ | H | C | 1 |
| 267 | 3,5-Cl$_2$-2-Pyr | 4-CF$_3$—Ph | H | H | H | CH$_3$ | H | O | 1 |
| 268 | 5-CF$_3$-3-Cl-2-Pyr | 4-Cl—Ph | H | H | H | CH$_3$ | H | O | 1 |
| 269 | 5-CF$_3$-3-Cl-2-Pyr | 4-CF$_3$—Ph | H | H | H | CH$_3$ | H | O | 1 |
| 270 | 2-Naph | 4-Cl—Ph | H | H | H | CH$_3$ | H | O | 1 |
| 271 | 6-Cl-2-Naph | 4-Cl—Ph | H | H | H | CH$_3$ | H | O | 1 |
| 272 | 6-Cl-2-Naph | 4-CF$_3$—Ph | H | H | H | CH$_3$ | H | O | 1 |
| 273 | 6-CF$_3$-2-Naph | 4-Cl—Ph | H | H | H | CH$_3$ | H | O | 1 |
| 274 | 6-CF$_3$-2-Naph | 4-CF$_3$—Ph | H | H | H | CH$_3$ | H | O | 1 |
| 275 | 6-CF$_3$O-2-Naph | 4-Cl—Ph | H | H | H | CH$_3$ | H | O | 1 |
| 276 | 6-CF$_3$S-2-Naph | 4-Cl—Ph | H | H | H | CH$_3$ | H | O | 1 |
| 277 | 6-CF$_3$SO$_2$-2-Naph | 4-Cl—Ph | H | H | H | CH$_3$ | H | O | 1 |
| 278 | 4-CF$_3$—Ph | 4-Cl—Ph | H | H | H | CH$_3$ | H | O | 1 b=1 |
| 279 | 4-Cl—Ph | 4-Cl—Ph | H | H | H | CH$_3$ | H | O | 1 b=1 |
| 280 | 4-Cl—Ph | Ph | H | H | H | CH$_3$ | H R$^7$=CH$_3$, b=1 | O | 1 |
| 281 | 4-CF$_3$—Ph | Ph | H | H | H | CH$_3$ | H R$^7$=CH$_3$, b=1 | O | 1 |
| 282 | 4-CF$_3$O—Ph | 4-CF$_3$—Ph | H | H | H | CH$_3$ | H | O | 1 |
| 283 | 2-F-4-Cl—Ph | 4-CF$_3$—Ph | H | H | H | CH$_3$ | H | O | 1 |
| 284 | 2-Cl-4-F—Ph | 4-CF$_3$—Ph | H | H | H | CH$_3$ | H | O | 1 |
| 285 | 2,4-F$_2$—Ph | 4-CF$_3$—Ph | H | H | H | CH$_3$ | H | O | 1 |
| 286 | 4-(PhC≡C)Ph | 4-Cl—Ph | H | H | H | CH$_3$ | H | O | 1 |

TABLE 2

($R^6=R^7=R^8=H$, $b=0$)

| No. | $Ar^1$ | $Ar^2$ | $(Q)_d$ | $R^3$ | $R^4$ | $R^5$ | W | a |
|---|---|---|---|---|---|---|---|---|
| 287 | Ph | 4-Cl—Ph | CH=CH | H | CH$_3$ | H | O | 1 |
| 288 | Ph | 4-Cl—Ph | C≡C | H | CH$_3$ | H | O | 1 |
| 289 | Ph | 4-CF$_3$O—Ph | C≡C | H | CH$_3$ | H | O | 1 |
| 290 | 4-Cl—Ph | 4-Cl—Ph | CH=CH | H | CH$_3$ | H | O | 1 |
| 291 | 4-Cl—Ph | 4-CF$_3$—Ph | C≡C | H | CH$_3$ | H | O | 1 |

TABLE 3

($R^6=R^7=R^8=H$, $b=0$, $d=0$)

| No. | $Ar^1$ | $Ar^2$ | $R^3$ | $R^4$ | $R^5$ | W | a |
|---|---|---|---|---|---|---|---|
| 292 | 4-Cl—Ph | Ph | H | CH$_3$ | H | O | 1 |
| 293 | 4-CF$_3$—Ph | 4-CF$_3$—Ph | H | CH$_3$ | H | O | 1 |
| 294 | 3-CF$_3$—Ph | 4-CF$_3$—Ph | H | CH$_3$ | H | O | 1 |
| 295 | 2-CF$_3$—Ph | 4-CF$_3$—Ph | H | CH$_3$ | H | O | 1 |
| 296 | 4-CF$_3$—Ph | 4-Cl—Ph | H | C$_2$H$_8$ | H | O | 1 |
| 297 | 4-CF$_3$—Ph | 4-Cl—Ph | H | H | H | O | 1 |
| 298 | 4-CF$_3$—Ph | 4-Cl—Ph | H | t-C$_4$H$_9$ | H | O | 1 |
| 299 | 4-CF$_3$—Ph | 4-Cl—Ph | H | (CH$_2$)$_4$ | | O | 1 |

TABLE 3-continued (R⁶=R⁷=R⁸=H, b=0, d=0)

| No. | Ar¹ | Ar² | R³ | R⁴ | R⁵ | W | a |
|---|---|---|---|---|---|---|---|
| 300 | 4-CF₃—Ph | 2-Cl—Ph | H | CH₃ | H | O | 4 |
| 301 | 4-Cl—Ph | 2,6-Cl₂-4-(Cl₂C=CHCH₂O)—Ph | H | CH₃ | H | O | 1 |
| 302 | 4-CF₃—Ph | 4-(t-C₄H₉C≡C)—Ph | H | CH₃ | H | O | 1 |
| 303 | 4-CF₃—Ph | 4-(PhC=-C)—Ph | H | CH₃ | H | O | 1 |
| 304 | 3,5-(CH₃)₂—Ph | 4-Cl—Ph | H | CH₃ | H | O | 1 |
| 305 | 4-CF₃—Ph | 4-Cl—Ph | H | CH₃ | H | O | 1 |
| | | | | | | b=1 | |
| 306 | 4-CF₃O—Ph | 4-CF₃—Ph | H | CH₃ | H | O | 1 |
| 307 | 3-CF₃O—Ph | 4-CF₃—Ph | H | CH₃ | H | O | 1 |
| 308 | 4-CF₃—Ph | Ph | H | CH₃ | H | O | 1 |
| | | | | | R⁷=CH₃, b=1 | | |
| 309 | 4-F—Ph | 4-CF₃—Ph | H | CH₃ | H | O | 1 |
| 310 | 2,4-Cl₂—Ph | 4-CF₃—Ph | H | CH₃ | H | O | 1 |
| 311 | 4-I—Ph | 4-CF₃—Ph | H | CH₃ | H | O | 1 |
| 312 | 4-NO₂—Ph | 4-CF₃—Ph | H | CH₃ | H | O | 1 |
| 313 | 4-C₂F₆—Ph | 4-CF₃—Ph | H | CH₃ | H | O | 1 |
| 314 | 4-CF₃—Ph | 4-CF₃O—Ph | H | CH₃ | H | O | 1 |
| 315 | 4-CH₃O—Ph | 4-CF₃—Ph | H | CH₃ | H | O | 1 |
| 316 | 4-CN—Ph | 4-CF₃—Ph | H | CH₃ | H | O | 1 |
| 317 | 2,6-Cl₂—Ph | 4-CF₃—Ph | H | CH₃ | H | O | 1 |
| 318 | 3,5-Cl₂—Ph | 4-CF₃—Ph | H | CH₃ | H | O | 1 |
| 319 | 2-Cl—Ph | 4-CF₃—Ph | H | CH₃ | H | O | 1 |
| 320 | 3-Cl—Ph | 4-CF₃—Ph | H | CH₃ | H | O | 1 |
| 321 | 4-Cl—Ph | 4-CF₃—Ph | H | CH₃ | H | O | 1 |
| 322 | 2-Cl-4-NO₂—Ph | 4-CF₃—Ph | H | CH₃ | H | O | 1 |
| 323 | 3-CH₃O—Ph | 4-CF₃—Ph | H | CH₃ | H | O | 1 |
| 324 | 3,4-Cl₂—Ph | 4-CF₃—Ph | H | CH₃ | H | O | 1 |
| 325 | 2-Cl-4-F—Ph | 4-CF₃—Ph | H | CH₃ | H | O | 1 |
| 326 | 4-CF₃—Ph | 4-CF₃—Ph | CH₃ | CH₃ | H | O | 1 |
| 327 | 2,5-Cl₂—Ph | 4-CF₃—Ph | H | CH₃ | H | O | 1 |
| 328 | 4-CF₃S—Ph | 4-CF₃—Ph | H | CH₃ | H | O | 1 |
| 329 | 2-CH₃—Ph | 4-CF₃—Ph | H | CH₃ | H | O | 1 |
| 330 | 3-CH₃—Ph | 4-CF₃—Ph | H | CH₃ | H | O | 1 |
| 331 | 4-CH₃—Ph | 4-CF₃—Ph | H | CH₃ | H | O | 1 |
| 332 | 2-CH₃O—Ph | 4-CF₃—Ph | H | CH₃ | H | O | 1 |
| 333 | 2,4-F₂—Ph | 4-CF₃—Ph | H | CH₃ | H | O | 1 |
| 334 | 5,6-Cl₂-3-Pyr | 4-Cl—Ph | H | CH₃ | H | O | 1 |
| 335 | 5,6-Cl₂-3-Pyr | 4-CF₃—Ph | H | CH₃ | H | O | 1 |
| 336 | 2-Cl-3-Pyr | 4-CF₃—Ph | H | CH₃ | H | O | 1 |
| 337 | 6-Cl-3-Pyr | 4-CF₃—Ph | H | CH₃ | H | O | 1 |
| 338 | 2-Naph | 4-CF₃—Ph | H | CH₃ | H | O | 1 |
| 339 | 4-COOCH₃—Ph | 4-CF₃—Ph | H | CH₃ | H | O | 1 |
| 340 | 3-Pyr | 4-CF₃—Ph | H | CH₃ | H | O | 1 |
| 341 | 2-Cl-6-CH₃-3-Pyr | 4-CF₃—Ph | H | CH₃ | H | O | 1 |
| 342 | 2,6-Cl₂-4-Pyr | 4-CF₃—Ph | H | CH₃ | H | O | 1 |
| 343 | 4-t-C₄H₉—Ph | 4-CF₃—Ph | H | CH₃ | H | O | 1 |
| 344 | 4-n-C₄H₉—Ph | 4-CF₃—Ph | H | CH₃ | H | O | 1 |
| 345 | 4-(CH₃)₂N—Ph | 4-CF₃—Ph | H | CH₃ | H | O | 1 |
| 346 | 4-CH₃COO—Ph | 4-CF₃—Ph | H | CH₃ | H | O | 1 |
| 347 | 4-CN—Ph | 4-CF₃—Ph | H | t-C₄H₉ | H | O | 1 |
| 348 | 2-CHF₂S-3-Pyr | 4-CF₃—Ph | H | CH₃ | H | O | 1 |
| 349 | 6-CHF₂O-3-Pyr | 4-CF₃—Ph | H | CH₃ | H | O | 1 |
| 350 | 2-F-4-CF₃—Ph | 4-CF₃—Ph | H | CH₃ | H | O | 1 |
| 351 | 4-CF₃CONH—Ph | 4-CF₃—Ph | H | CH₃ | H | O | 1 |
| 352 | 4-(3-Cl-5-CF₃-2-Pyr)O—Ph | 4-CF₃—Ph | H | CH₃ | H | O | 1 |
| 353 | 2,4-Cl₂—Ph | 4-CF₃—Ph | H | t-C₄H₉ | H | O | 1 |
| 354 | 2,4-Cl₂—Ph | 4-CF₃—Ph | H | i-C₃H₇ | H | O | 1 |
| 355 | 4-CN—Ph | 4-CF₃—Ph | H | i-C₃H₇ | H | O | 1 |
| 356 | 2,4-Cl₂—Ph | 4-CF₃—Ph | H | CH₃ | CH₃ | O | 1 |
| 357 | 4-CN—Ph | 4-CF₃—Ph | H | CH₃ | CH₃ | O | 1 |
| | | | | | | Rf=H | |
| 358 | 4-CN—Ph | 4-CF₃—Ph | H | CH₃ | CH₃ | O | 1 |
| | | | | | | Rf=L | |
| 359 | 2-Pyr | 4-CF₃—Ph | H | CH₃ | H | O | 1 |
| 360 | 2-CH₃S-3-Pyr | 4-CF₃—Ph | H | CH₃ | H | O | 1 |
| 361 | 2-CH₃SO₂-3-Pyr | 4-CF₃—Ph | H | CH₃ | H | O | 1 |
| 362 | 3,5-Cl₂-2-Pyr | 4-CF₃—Ph | H | CH₃ | H | O | 1 |
| 363 | 3-Cl-5-CF₃-2-Pyr | 4-CF₃—Ph | H | CH₃ | H | O | 1 |
| 364 | 4-CF₃SO₂NH—Ph | 4-CF₃—Ph | H | CH₃ | H | O | 1 |
| 365 | 4-CN—Ph | 4-CF₃—Ph | CH₃ | CH₃ | H | O | 1 |

TABLE 3-continued ($R^6=R^7=R^8=H$, b=O, d=O)

| No. | Ar$^1$ | Ar$^2$ | R$^3$ | R$^4$ | R$^5$ | W | a |
|---|---|---|---|---|---|---|---|
| 366 | 4-CF$_3$SO$_2$—Ph | 4-CF$_3$—Ph | H | CH$_3$ | H | O | 1 |
| 367 | 1-Naph | 4-CF$_3$—Ph | H | CH$_3$ | H | O | 1 |
| 368 | 4-n-C$_3$H$_7$S—Ph | 4-CF$_3$—Ph | H | CH$_3$ | H | O | 1 |
| 369 | 4-C$_2$F$_5$S—Ph | 4-CF$_3$—Ph | H | CH$_3$ | H | O | 1 |

In table 1, Table 2 and Table 3, Ph represents phenyl group, Pyr represents pyridyl group, Naph represents naphtyl group and c-represents alicyclic hydrocarbon.

Table 4 shows physical properties of the compound listed in the Table 1, Table 2 and Table 3.

TABLE 4

| No. | Physical properties (melting point, refractive index, NMR(CDCl$_3$/TMS), δ value (ppm)) |
|---|---|
| 1 | m.p. 101° C. |
| 2 | m.p. 152° C. |
| 3 | m.p. 121° C. |
| 9 | nD 1.542(21° C.) |
| 10 | paste NMR: 1.65(s.3H), 1.51–1.72(m.4H), 1.80–2.12(m.4H), 3.69(s.2H), 3.95–4.03(m.2H), 5.59(br.1H), 6.8–6.9(m.2H), 7.1–7.40(m.6H). |
| 11 | paste NMR: 1.74(s.3H), 2.06(m.2H), 3.61(m.2H), 3.55–3.80(m.2H), 4.28(m.2H), 7.06(br.1H), 7.12(d.2H), 7.18–7.24(m.2H), 7.25–7.40(m.4H). |
| 12 | m.p. 127–133° C. |
| 13 | m.p. 138–139° C. |
| 14 | m.p. 98–99° C. (Rf = H) |
| 15 | paste (Rf = L) NMR: 1.32(d.3H), 1.75(s.3H), 3.72(s.2H), 4.60–4.70(m.1H), 5.97(br.1H), 6.76(d.2H), 7.20–7.42(m.6H). |
| 16 | paste (Rf = L) NMR: 0.83(t.3H), 1.20–2.00(m.4H), 3.66(s.2H), 4.82(br.1H), 5.87(br.1H), 6.86(d.2H), 7.15–7.30(m.6H). |
| 17 | paste (Rf = H) NMR: 0.89(t.3H), 1.20–2.00(m.4H), 3.40–3.57(m.2H), 5.02(br.1H), 5.70(br.1H), 6.73(d.2H), 7.05–7.30(m.6H). |
| 18 | m.p. 125–128° C. (Rf = H) |
| 19 | paste (Rf = L) NMR: 0.81(t.3H), 1.10–1.80(m.6H), 3.67(s.2H), 4.75–4.82(m.1H), 5.79(br.1H), 6.85(d.2H), 7.18–7.40(m.6H). |
| 20 | m.p. 97° C. |
| 21 | m.p. 131° C. |
| 22 | m.p. 107–110° C. |
| 23 | m.p. 123–126° C. |
| 24 | m.p. 125–126° C. |
| 25 | paste NMR: 1.08(s.9H), 3.68–3.82(m.2H), 4.36–4.47(m.2H), 5.69(br.1H), 6.75(d.2H), 7.18–7.46(m.6H). |
| 26 | m.p. 78–84° C. |
| 27 | paste NMR: 1.94(s.3H), 3.20(s.3H), 3.83(m.2H), 4.46(s.2H), 6.82(d.2H), 7.12–7.30(m.5H), 7.37(d.1H). |
| 28 | m.p. 110–112° C. |
| 29 | m.p. 118–120° C. |
| 30 | m.p. 72–74° C. |
| 41 | m.p. 132–133° C. |
| 42 | m.p. 116–117° C. |
| 44 | m.p. 134–143° C. (Rf = H) |
| 45 | paste (Rf = L) NMR: 1.31(d.3H), 1.74(s.3H), 3.54(s.2H), 4.62–4.70(m.1H), 6.12(br.1H), 6.76(d.2H), 7.06–7.30(m.6H). |
| 46 | paste (Rf = H) NMR: 0.92(t.3H), 1.20–2.00(m.4H), 3.29(s.2H), 5.02–5.12(s.1H), 5.45(m.1H), 6.75(d.2H), 7.13–7.26(m.6H). |
| 47 | paste (Rf = L) NMR: 0.85(t.3H), 1.20–2.00(m.4H), 3.49(s.2H), 4.78–4.81(m.1H), 5.81(br.1H), 6.84(d.2H), 7.15–7.30(m.6H). |
| 48 | m.p. 134–136° C. |
| 49 | m.p. 103–104° C. |
| 50 | paste NMR: 1.65(s.3H), 1.50–2.10(m.6H), 3.54(s.2H), 3.88–3.93(s.2H), 5.52(br.1H), 6.79(d.2H), 7.10–7.30(m.6H). |
| 51 | m.p. 96–99° C. |
| 52 | m.p. 121–122° C. |
| 53 | m.p. 121–124° C. |
| 54 | paste NMR: 1.07(s.9H), 3.52–3.66(m.2H), 4.33–4.52(m.2H), 5.55(br.1H), 6.78(d.2H), 7.10–7.33(m.6H). |
| 55 | paste NMR: 1.20–2.00(m.8H), 3.49(s)/3.52(s)(2H), 4.35(br)/4.85(br)(1H), 5.62(br)/5.95(br)(1H), 6.70–6.80(m.2H), 7.00–7.30(m.6H). |
| 56 | m.p. 113–114° C. |
| 57 | m.p. 132–135° C. |
| 58 | m.p. 142° C. |
| 59 | m.p. 169° C. |
| 60 | m.p. 126–127° C. |
| 61 | paste NMR: 1.64(s.3H), 1.52–2.15(m.8H), 3.53(s.3H), 3.95–4.03(m.2H), 5.59(br.1H), 6.86–6.95(m.2H), 7.12–7.40(m.6H). |
| 62 | m.p. 126–127° C. |
| 63 | m.p. 122–128° C. |
| 64 | m.p. 152° C. |
| 65 | m.p. 87–89° C. |
| 66 | m.p. 95° C. |
| 67 | m.p. 153° C. |
| 68 | paste NMR: 1.64(s.3H), 1.50–2.10(m.6H), 3.54(s.2H), 3.87–3.93(m.2H), 5.47(br.1H), 6.80(d.2H), 7.15–7.40(m.6H). |
| 69 | m.p. 124–141° C. |
| 70 | paste NMR: 0.85(t)/0.92(t)(3H), 1.20–2.00(m.4H), 3.21–3.36(m)/3.49(s)(2H), 4.74–4.80(br)/5.04–5.12(br)(1H), 5.41(br)/5.76(br)(1H), 6.70–7.30(m.8H). |
| 71 | m.p. 124–130° C. (Rf = H) |
| 73 | m.p. 126–127° C. |
| 74 | m.p. 104–105° C. |
| 75 | m.p. 140° C. |
| 76 | m.p. 142° C. |
| 77 | paste NMR: 1.07(s.9H), 3.52–3.66(m.2H), 4.34–4.50(m.2H), 5.57(br.1H), 6.75(d.2H), 7.12–7.37(m.6H). |
| 79 | paste NMR: 1.20–2.10(m.8H), 3.48(s)/3.50(s)(2H), 4.32(br)/4.84(br)(1H), 5.60(br)/5.90(br)(1H), 6.67–6.75(m.2H), 7.00–7.30(m.6H). |
| 80 | paste NMR: 1.91(s.3H), 3.11(s.3H), 3.70(s.2H), 4.39–4.51(m.2H), 6.78(d.2H), 7.09((d.2H), 7.22–7.26(m.4H). |
| 81 | m.p. 83–84° C. |
| 82 | m.p. 57–63° C. |

TABLE 4-continued

| No. | Physical properties (melting point, refractive index, NMR(CDCl$_3$/TMS), δ value (ppm)) |
|---|---|
| 83 | m.p. 114–117° C. |
| 84 | m.p. 105–108° C. |
| 85 | m.p. 148–149° C. (Rf = H) |
| 86 | m.p. 152–154° C. (Rf = L) |
| 88 | m.p. 145–146° C. |
| 89 | m.p. 123° C. |
| 90 | m.p. 135–137° C. |
| 91 | m.p. 96–97° C. |
| 92 | m.p. 160–161° C. |
| 94 | m.p. 127–130° C. |
| 95 | m.p. 132–133° C. |
| 96 | m.p. 120–121° C. |
| 97 | m.p. 96–100° C. |
| 99 | m.p. 114–115° C. |
| 100 | m.p. 126–127° C. |
| 102 | m.p. 162° C. |
| 103 | m.p. 159–163° C. |
| 105 | m.p. 130° C. |
| 108 | m.p. 85–86° C. |
| 109 | paste NMR: 1.80(s.3H), 3.03(s.3H), 3.58(s.2H), 4.32(dd.2H), 5.88(br.1H), 6.96(d.2H), 7.18(s.2H), 7.32(d.2H), 7.86(d.2H). |
| 114 | m.p. 91–92° C. |
| 116 | paste NMR: 1.81(s.3H), 3.59(s.2H), 4.36–4.45(m.2H), 5.68(br.1H), 7.03–7.10(m.2H), 7.18(d.2H), 7.33(d.2H), 7.76(d.1H), 7.99(d.1H). |
| 117 | m.p. 102–104° C. |
| 118 | paste NMR: 1.81(s.3H), 3.59(s.2H), 4.30–4.45(m.2H), 5.66(br.1H), 7.04–7.10(m.2H), 7.17(d.2H), 7.33(d.2H), 7.75(d.1H), 7.99(d.1H). |
| 120 | m.p. 160–161° C. |
| 121 | m.p. 88–90° C. |
| 122 | m.p. 125–126° C. |
| 123 | m.p. 93–94° C. |
| 124 | m.p. 141–142° C. |
| 125 | m.p. 175–176° C. |
| 126 | nD 1.511(26° C.) |
| 125 | m.p. 88–89° C. |
| 128 | m.p. 87–89° C. |
| 129 | paste NMR: 1.81(s.3H), 3.59(s.2H), 3.93(d.2H), 4.35(dd.2H), 5.80(br.1H), 5.98(t.1H), 6.98(d.2H), 7.19(d.2H), 7.33(d.2H), 7.82(d.2H). |
| 130 | m.p. 127–128° C. |
| 133 | m.p. 156–158° C. |
| 134 | m.p. 146–147° C. |
| 141 | m.p. 159–160° C. |
| 142 | m.p. 156–157° C. |
| 143 | m.p. 128–129° C. |
| 144 | m.p. 144° C. |
| 145 | m.p. 137–139° C. |
| 146 | m.p. 107–109° C. |
| 147 | m.p. 112–113° C. |
| 148 | m.p. 138–140° C. |
| 149 | m.p. 108–110° C. |
| 150 | m.p. 128–129° C. |
| 151 | m.p. 108–110° C. |
| 152 | m.p. 136° C. |
| 153 | m.p. 146° C. |
| 154 | m.p. 146–147° C. |
| 156 | m.p. 142–143° C. |
| 157 | m.p. 98–99° C. |
| 158 | m.p. 123–124° C. |
| 160 | m.p. 117–118° C. |
| 161 | m.p. 110–112° C. |
| 163 | nD 1.521(21° C.) |
| 164 | m.p. 126–127° C. |
| 165 | m.p. 115° C. |
| 166 | m.p. 129–131° C. |
| 167 | paste (Rf = H) NMR: 0.91(t.3H), 1.20–1.90(m.4H), 3.18–3.38(m.2H), 3.78(s.3H), 5.04–5.12(m.1H), 5.39(br.1H), 6.70–6.82(m.6H), 7.20(d.2H). |
| 168 | paste (Rf = L) NMR: 0.84(t.3H), 1.20–1.90(m.4H), 3.41–3.55(m.2H), 3.79(s.3H), 4.72–4.80(m.1H), 5.72(br.1H), 6.78–6.85(m.4H), 7.05(d.2H), 7.24(d.2H). |
| 169 | m.p. 121–126° C. (Rf = H) |
| 170 | paste NMR: 1.61(s.3H), 1.45–2.10(m.6H), 3.52(s.2H), 3.78(s.3H), 3.85–3.93(m.2H), 5.44(br.1H), 6.78(d.1H), 6.87(d.2H), 7.15(d.2H), 7.28(d.2H). |
| 171 | m.p. 104–107° C. |
| 172 | paste NMR: 0.95(t.3H), 1.35–1.55(m.2H), 1.95–2.05(m.2H), 3.53(s.2H), 3.80(s.3H), 4.19–4.33(m.2H), 5.63(br.1H), 6.74(d.2H), 6.87(d.2H), 7.11(d.2H), 7.23(d.2H). |
| 173 | m.p. 114–117° C. |
| 174 | m.p. 119–122° C. |
| 175 | paste NMR: 1.03(s.9H), 3.49–3.64(m.2H), 3.81(s.3H), 4.32–4.50(m.2H), 5.58(br.1H), 6.77(d.2H), 6.91(d.2H), 7.13(d.2H), 7.24(d.2H). |
| 176 | paste NMR: 1.20–2.10(m.8H), 3.43–3.55(m.2H), 3.73(s)/3.87(s)(3H), 4.26(br)/4.80(br)(1H), 5.61(br)/5.86(br)(1H), 6.65–7.25(m.8H). |
| 184 | m.p. 87–88° C. |
| 186 | m.p. 130° C. |
| 187 | m.p. 119° C. |
| 188 | m.p. 128–130° C. |
| 189 | m.p. 145–147° C. |
| 190 | m.p. 80–81° C. |
| 191 | m.p. 88–90° C. |
| 192 | m.p. 112–113° C. |
| 193 | m.p. 108–109° C. |
| 195 | m.p. 95–96° C. |
| 196 | m.p. 105–111° C. |
| 197 | m.p. 82–85° C. |
| 199 | m.p. 135–136° C. |
| 200 | m.p. 85–87° C. |
| 207 | m.p. 59–60° C. |
| 209 | paste NMR: 1.83(s.3H), 3.67(s.3H), 4.30–4.50(m.2H), 5.82(br.1H), 7.03–7.05(m.2H), 7.37(d.2H), 7.61(d.2H), 7.74(d.1H), 7.98(d.1H) |
| 210 | m.p. 90–91° C. |
| 211 | paste NMR: 1.83(s.3H), 3.68(s.2H), 4.30–4.46(m.2H), 5.73(br.1H), 7.03–7.10(m.2H), 7.38(d.2H), 7.61(d.2H), 7.75(d.1H), 7.98(d.1H). |
| 213 | m.p. 103–105° C. |
| 216 | m.p. 87–88° C. |
| 218 | m.p. 159–161° C. |
| 219 | m.p. 177–178° C. |
| 220 | m.p. 140–143° C. |
| 221 | m.p. 133–137° C. |
| 223 | m.p. 88–89° C. |
| 224 | m.p. 86–88° C. |
| 229 | nD 1.554(26° C.) |
| 230 | m.p. 131–132° C. |
| 231 | m.p. 100° C. |
| 232 | nD 1.543(21° C.) |
| 233 | m.p. 123–124° C. |
| 234 | m.p. 141° C. |
| 235 | m.p. 130–131° C. |
| 236 | m.p. 154–155° C. |
| 237 | m.p. 94° C. |
| 238 | m.p. 85° C. |
| 243 | m.p. 104–106° C. |
| 244 | m.p. 136° C. |
| 245 | m.p. 87° C. |
| 253 | m.p. 97–99° C. |
| 269 | m.p. 137–139° C. |
| 270 | m.p. 138° C. |
| 278 | m.p. 71–73° C. |
| 279 | m.p. 103–106° C. |
| 280 | m.p. 106–108° C. |
| 281 | m.p. 114–117° C. |

TABLE 4-continued

| No. | Physical properties (melting point, refractive index, NMR(CDCl₃/TMS), δ value (ppm)) |
|---|---|
| 282 | m.p. 121–125° C. |
| 283 | m.p. 105–106° C. |
| 284 | m.p. 141–143° C. |
| 285 | m.p. 115–120° C. |
| 286 | m.p. 162–164° C. |
| 287 | m.p. 140–142° C. |
| 288 | paste NMR: 1.89(s.3H), 4.27(s.2H), 6.52(br.1H), 7.26(d.2H), 7.30–7.60(m.5H). |
| 289 | paste NMR: 1.91(s.3H), 4.31(s.2H), 6.28(br.1H), 6.96(d.2H), 7.35–7.60(m.5H). |
| 290 | m.p. 163–164° C. |
| 291 | paste NMR: 1.92(s.3H), 4.37(s.2H), 6.33(br.1H), 7.02(d.2H), 7.35(d.2H), 7.47(d.2H), 7.59(d.2H), |
| 292 | m.p. 135–140° C. |
| 293 | m.p. 135–136° C. |
| 294 | m.p. 115° C. |
| 295 | m.p. 128–130° C. |
| 296 | m.p. 118–119° C. |
| 297 | m.p. 134–140° C. |
| 298 | m.p. 125–135° C. |
| 299 | paste NMR: 1.40–2.30(m.8H), 4.62/4.99(br.s.1H), 6.38/6.62(br.s.1H), 6.99–6.97(m.2H), 7.16–7.30(m.2H), 7.62–7.82(m.4H) |
| 300 | paste NMR: 1.50–2.35(m.8H), 1.84(s.3H), 4.12(q.2H), 6.31(br.s.1H), 6.92(d.2H), 7.21(dd.1H), 7.34(dd.1H), 7.66(d.2H), 7.85(d.2H) |
| 301 | m.p. 135–136° C. |
| 302 | m.p. 217–218° C. |
| 303 | m.p. 195–198° C |
| 304 | m.p. 129–130° C. |
| 305 | m.p. 106–108° C. |
| 306 | m.p. 132–136° C. |
| 307 | m.p. 92° C. |
| 308 | m.p. 72–77° C. |
| 309 | m.p. 135–137° C. |
| 310 | m.p. 120–122° C. |
| 311 | m.p. 155–160° C. |
| 312 | m.p. 96–97° C. |
| 313 | m.p. 127–129° C. |
| 314 | m.p. 127–128° C. |
| 315 | m.p. 161–166° C. |
| 316 | paste NMR: 1.98(s.3H), 4.45(q.2H), 6.65(br.s.1H), 7.03(d.2H), 7.58(d.2H), 7.76(d.2H), 7.88(d.2H) |
| 317 | paste NMR: 1.98(s.3H), 4.47(s.2H), 6.33(br.s.1H), 7.01(d.1H), 7.32(m.4H), 7.57(d.2H) |
| 318 | paste NMR: 1.97(s.3H), 4.44(q.2H), 6.56(br.s.1H), 7.02(d.2H), 7.53(m.1H), 7.61(d.2H), 7.63(s.2H) |
| 319 | m.p. 122–123° C. |
| 320 | m.p. 149–154° C. |
| 321 | m.p. 144–145° C. |
| 322 | m.p. 205–208° C. |
| 323 | m.p. 142–144° C. |
| 324 | m.p. 147–148° C. |
| 325 | m.p. 130–132° C. |
| 326 | m.p. 98–100° C. |
| 327 | m.p. 118–121° C. |
| 328 | m.p. 140–141° C. |
| 329 | m.p. 137–140° C. |
| 330 | m.p. 166–168° C. |
| 331 | m.p. 187–190° C. |
| 332 | m.p. 85–88° C. |
| 333 | m.p. 127–128° C. |
| 334 | m.p. 171–173° C. |
| 335 | m.p. 158–159° C. |
| 336 | m.p. 150–154° C. |
| 337 | m.p. 137–140° C. |
| 338 | m.p. 219–222° C. |
| 339 | m.p. 126–130° C. |
| 340 | m.p. 133–134° C. |
| 341 | paste NMR: 1.99(s.3H), 2.50(s.3H), 4.41(d.1H), 4.49(d.1H), 7.03(d.2H), 7.25(d.2H), 7.30(br.s.1H), 7.59(d.2H), 8.18(d.1H) |
| 342 | m.p. 119–123° C. |
| 343 | m.p. 249–251° C. |
| 344 | m.p. 184–187° C. |
| 345 | m.p. 254–257° C. |
| 346 | m.p. 170–173° C. |
| 347 | m.p. 111–114° C. |
| 348 | paste NMR: 1.97(s.3H), 4.40(d.1H), 4.47(d.1H), 6.65(br.s.1H), 7.03(d.2H), 7.19–7.23(m.1H), 7.59(d.2H), 7.62(t.1H), 7.80–7.91(m.1H), 8.55–8.57(m.1H) |
| 349 | paste NMR: 1.94(s.3H), 4.41(dd.2H), 6.71(br.s.1H), 6.93(d.1H), 7.00(d.2H), 7.45(t.2H), 7.55(d.2H), 8.11–8.14(m.1H), 8.56(d.1H) |
| 350 | m.p. 118–119° C. |
| 351 | m.p. 161–163° C. |
| 352 | m.p. 132–139° C. |
| 353 | m.p. 149–151° C. |
| 354 | paste NMR: 1.22–1.29(m.6H), 2.76(m.1H), 4.60(q.2H), 6.70(br.s.1H), 6.99(d.2H), 7.34(m.1H), 7.43(m.1H), 7.48(d.2H), 7.70(d.2H) |
| 355 | paste NMR: 1.20–1.32(m.6H), 2.81(m.1H), 4.60(q.2H), 6.43(br.s.1H), 6.98(d.2H), 7.55(d.2H), 7.76–7.86(m.4H), 7.70(d.2H) |
| 356 | paste NMR: 1.52–1.57(m.3H), 1.91/1.93(s.3H), 5.03/5.26(q.2H), 6.76/6.96(br.s.1H), 6.98–7.10(m.2H), 7.26–7.79(m.5H) |
| 357 | m.p. 210–213° C. (Rf = H) |
| 358 | m.p. 206–208° C. (Rf = L) |
| 359 | m.p. 90–91° C. |
| 360 | m.p. 137–140° C. |
| 361 | m.p. 132° C. |
| 362 | paste NMR: 1.99(s.3H), 4.43(d.2H), 4.49(d.1H), 7.04(d.2H), 7.57(d.2H), 7.89(d.1H), 8.25(br.s.1H), 8.41(d.1H) |
| 363 | paste NMR: 1.99(s.3H), 2.61(s.3H), 4.46(s.2H), 7.02–7.09(m.4H), 7.58(d.2H), 7.92–7.96(m.1H), 8.53–8.55(m.1H) |
| 364 | m.p. 200–202° C. |
| 365 | m.p. 137–142° C. |
| 366 | m.p. 130–133° C. |
| 367 | m.p. 138–140° C. |
| 368 | m.p. 141–142° C. |
| 369 | m.p. 138–139° C. |

In Table 3 or 4, Rf-H or Rf-L indicates stereoisomers; Rf-H indicates an isomer having a high Rf values from among the stereoisomers, and Rf-H indicates isomers having a low Rf value.

Hereafter, typical examples, formulation examples, and test examples of the present invention.

EXAMPLES

Example 1

Production of Compound No. 63

4-Chlorophenol (2.56 g), bromoacetaldehyde dimethylacetal acetal (3.4 g), anhydrous pottasium carbonate (2.76 g) and a catalytic amount of sodium iodide were added to DMF (dimethylformamide)(20 ml) and heated under reflux for 3 hours. Water was added to the reaction mixture, which was then extracted with ethyl acetate and the organic layer was dried over anhydrous sodium sulfate, and the solvent was distilled off the residue was purified by silica gel column chromatography (ethyl acetate-hexane) to obtain 4-chlorophenoxyacetaldehyde dimethylacetal (2.37 g).

4-Chlorophenoxyacetaldehyde dimethylacetal (1.0 g) was dissolved in acetone (10 ml), to which 2N hydrochloric acid (1.0 g) was added, and the mixture was heated under reflux for 8 hours. After the reaction mixture was concentrated, water was added and the mixture was extracted with ethyl acetate. The extracts were dried over anhydrous sodium sulfate. The solvent was distilled off to obtain 4-chlorophenoxyacetaldehyde as a crude product.

Crude 4-chlorophenoxyacetaldehyde (0.5 g), sodium cyanide (0.17 g) and ammonium chloride (0.27 g) were added into 28% ammonia water (20 ml) and stirred for 2 days. To the reaction solution was added ethyl acetate and the mixture was washed with water and dried over anhydrous sodium sulfate and the solvent was distilled off. The resulting oil was dissolved in THF (tetrahydrofuran)(5 ml) and added with 4-chlorophenylacetyl chloride (0.38 g) and triethylamine (0.22 g). The mixture was stirred at room temperature for 6 hours. Water was added to the reaction mixture, which was extracted with ethyl acetate and the extracts were dried over anhydrous sodium sulfate and the solvent was distilled off. The residue was purified by silica gel column chromatography (ethyl acetate-hexane) to obtain the intended compound (0.21 g; yield 24%; m.p. 122–128° C.).

Example 2
Production of Compound No. 64

4-Chlorophenol (10 g), chloroacetone (10.8 g), anhydrous potassium carbonate (12.9 g) and potassium iodide (1.3 g) were added to acetone (100 ml) and heated under reflux for 6 hours. The reaction mixture was filtered and the filtrate was concentrated to obtain 4-chlorophenoxyacetone (14 g).

4-Chlorophenoxyacetone (6.0 g), sodium cyanide (1.91 g) and ammonium chloride (2.6 g) were added into 28% ammonia water (20 ml) and stirred vigorously for twenty-four hours. To the reaction mixture was added ethyl acetate and the mixture was washed with water and dried over anhydrous sodium sulfate and the solvent was distilled off to obtain 2-amino-2-methyl-3-(4-chlorophenoxy) propanenitrile (6.5 g).

4-Chlorophenylacetic acid (0.4 g) was added to thionyl chloride (1 ml) and heated under reflux for 1 hour and excess thionyl chloride was distilled off under reduced pressure. The resulting acid chloride was added to THF solution (5 ml) in which 2-amino-2-methyl-3-(4-chlorophenoxy) propanenitrile (0.49 g) and triethylamine (0.26 g) were dissolved under ice cooling and stirred at room temperature for 3 hours. To the reaction mixture was added water and the mixture was extracted with ethyl acetate. The extracts were dried over anhydrous sodium sulfate and the solvent was distilled off. The solid residue was washed with hexane-ether to obtain the intended compound (0.56 g; yield 66%; m.p. 152° C.).

Example 3
Production of Compound No. 81

4-Chlorophenoxyacetone (1.84 g), sodium cyanide (0.5 g), ammonium chloride (0.9 g) were dissolved in methanol (10 ml), to which an excess amount of an aqueous ethylamine solution was added. The mixture was stirred at room temperature for 2 days. After completion of the reaction, the solvent was distilled off and the residue was extracted with ethylacetate, followed by a common procedure to obtain 2-ethylamino-2-methyl-3-(4-chlorophenoxy)propanenitrile (2.2 g).

2-Ethylamino-2-methyl-3-(4-chlorophenoxy) propanenitrile (0.5 g) and 4-chlorophenylacetyl chloride (0.38 g) were dissolved in THF (10 ml), to which pyridine (0.16 g) was added and the mixture was heated under reflux for 5 hours. After cooling to room temperature, insoluble matter was filtered and the solvent was distilled off. The resulting oil was purified by silica gel column chromatography (ethyl acetate-hexane) to obtian the intended compound (0.16 g; yield 20%; m.p. 83–84° C.).

Example 4
Production of Compound No. 166

4-Methoxyphenylacetic acid (0.67 g) and 2-chloro-1-methylpyridinium iodide (1.10 g) were suspended in THF (10 ml), to which triethylamine (0.50 g) was dropwise added at room temperature. After stirring for 5 minutes, 2-amino-2-methyl-3-(4-chlorophenoxy)butanenitrile (0.90 g) was added and the mixture was stirred for 6 hours. After completion of the reaction, insoluble matter was filtered and the solvent was distilled off. The residue was purified by silica gel column chromatography (ethyl acetate-hexane) to obtain the intended compound (0.78 g; yield 52%; m.p. 129–131° C.).

Example 5
Production of Compound No. 253

2-(5-Trifluoromethyl-2-pyridyl)acetic acid hydrochloride (0.74 g), 2-amino-2-methyl-3-(4-trifluoromethylphenoxy) propanenitrile (0.65 g), 2-chloro-1-methylpyridinium iodide (1.17 g) and triethylamine (0.93 g) were added to acetonitrile (10 ml) and heated under reflux for 6 hours. To the reaction mixture was added water and the mixture was extracted with ethyl acetate and dried over anhydrous sodium sulfate. Thereafter, the solvent was distilled off. The residue was purified by silica gel column chromatography (ethyl acetate-hexane) to obtain the intended compound (0.34 g; yield 28%; m.p. 97–99° C.).

Example 6
Production of Compound No. 288

3-Phenylacetylenecarboxylic acid (0.28 g), 2-amino-2-methyl-3-(4-chlorophenoxy)propanenitrile (0.40 g) and dicyclohexylcarbodiimide (0.41 g) were dissolved in dichloromethane (5 ml) and the solution was heated under reflux for 8 hours. The reaction mixture was filtered and the filtrate was concentrated. The residue was purified by silica gel column chromatography (ethyl acetate-hexane) to obtain the intended compound (0.11 g; yield 17%; paste).

The agricultural and horticultural insecticide containing the aminoacetonitrile derivative of the formula (I) of the invention as an active ingredient is suitable for controlling various pests in agriculture, forestry, horticulture, stored products as well as sanitary vermin or nematoda which are harmful for paddy rice, fruit trees, vegetables, other crops and flowers. It has strong insecticidal effect on pests, for example, injurious insects of Lepidoptera such as summer fruit tortrix (*Adoxophyes orana fasciata*), smaller tea tortrix (Adoxophyes sp.), Manchurian fruit moth (*Grapholita inopinata*), oriental fruit moth (*Grapholita molesta*), soybean pod borer (*Leguminivora glycinivorella*), mulberry leafroller (Olethreutesmori), tea leafrokker (*Caloptilia thevivora*), *Caloptilia zachrysa*, apple leafminer (*Phyllonorycter ringoniella*), pear barkminer (*Spulerrina astaurota*), common cabbage worm (*Piers rapae crucivora*), corn earworm, cotton bollworm, tabacco budworm and tomato grub (Heliothis sp.), codling moth (*Laspey resia pomonella*), diamondback moth (*Plutella xylostella*), apple fruit moth (*Argyresthia conjugella*), peach fruit moth (*Carposina niponesis*), rice stem borer (*Chilo suppressalis*), rice leafroller (*Cnaphalocrocis medinalis*), tabacco moth (*Ephestia elutella*), mulberry pyralid (*Glyphodes pyloalis*), yellow rice borer (*Scirpophaga incertulas*), rice skipper (*Parnara guttata*), rice armyworm (*Pseudaletia separata*), pink birer (*Sesamia inferens*), common cutworm (*Spodoptera litura*), beet armyworm (*Spodoptera exigua*); injurious insects of Hemiptera such as aster leafhopper (*Macrosteles fascifrons*), green rice leafhopper (*Nephotettix cincticeps*), brown rice planthopper (*Nilaparvata lugens*), whitebacked rice planthopper (*Sogatella furcifera*), citrus psylla (*Diaphorina citri*), grape whitefly (*Aleurolobus taonabae*), sweet potato whitefly (*Bemisia tabaci*), greenhouse whitefly (*Trialeurodes vaporariorum*), turnip aphid (*Lipaphis erysimi*), green peach aphid (*Myzus persicae*), Indianwax scale (*Ceroplastes ceriferus*), cottony cutrus scale (*Pulvinaria aurantii*), camphorscale (*Pseudaonidia duplex*), San Jose scale (*Comstockaspis perniciosa*), arrowhead scale (*Unaspis yanonesis*); injurious insects of Coleoptera such as soybean beetle (*Anomala rufocuprea*), Japanese beetle (*Popillia japonica*), tabacco beetle (*Lasioderma serricorne*), powderpost beetle (*Lyctus brunneus*), twenty-eight-spotted ladybird (*Epilachna vigintiotopunctata*), adzuki bean weevil (*Callosobruchus chinensis*), vegetable weevil (*Listroderes costirostris*), maize weevil (*Sitophilus zeamais*), boll weevil (*Anthonomus gradis gradis*), rice water weevil (*Lissorhoptrus oryzophilus*), cucurbit leaf beetle (*Aulacophora femoralis*), rice leaf beetle (*Oulema oryzae*), striped flea beetle (*Phyllotreta striolata*), pine shoot beetle (*Tomicus piniperda*), Colorado potate beetle (*Leptinotarsa decemlineata*), Mexican bean beetle (*Epilachna varivestis*), corn root worm (Diabrotica sp.); injurious insects of Diptera such as melon fly (*Dacus(Zeugodacus)cucurbitae*), oriental fruit fly (*Dacus(Bactrocera)dorsalis*), rice leafminer (*Agromyza oryzae*), onion maggot (*Delia antiqua*), seedcorn maggot (*Delia platura*), soybean pod gall midge (Asphondylia sp.), house fly (*Musca domestica*), house mosquito (*Culex pipiens*); injurious insects of Tylenchida such as root-lesion nematode (Pratylenchussp.), potatocyst nematode (*Globodera rostochiensis*), root-knot nematode (Meloidogyne sp.), citrus nematode (*Tylenchulus semipenetrans*), *Aphelenchus avenae,* chrysanthemumfoliar nematode (*Aphelenchoides ritzemabosi*).

The agricultural and horticultural insecticide containing the aminoacetonitrile derivative of the formula (I) of the invention has remarkable controlling effect on the above-mentioned pests harmful to paddy field crops, farm crops, fruit trees, vegetables, and other crops and flowers so that treatment of paddy field water, stems and leaves or soil, such as paddy field, farm, fruit trees, vegetables, other crops, and flowers in a good timing when emergence of pests is expected and before emergence of pests or after their emergence is confirmed will exhibit the desired effects of the agricultural and horticultural insecticide of the present invention.

The agricultural and horticultural insecticide of the present invention is generally formulated in appropriate formulation convenient for use according to conventional methods for the production of agricultural chemicals before it can be used.

That is, the aminoacetonitrile derivative of the formula (I) may be mixed in an appropriate amount with a suitable inert carrier and, as required, with an adjuvant to conduct dissolution, dispersion, suspension, mixing, dipping, adsorption or absorption and the mixture be formulated into a suspension, an emulsion, a liquid, a wettable powder, a granule, a dust, tablets or the like.

The inert carrier which can be used in the present invention may be any of solids or liquids. Materials which can be used as solid carriers include, for example, soybean flour, cereal flour, wood flour, bark flour, sawdust, tobacco stalk flour, walnut shell flour, wheat bran, cellulose fiber, residue after formation of a plant extract, synthetic polymers such as pulverized synthetic resin, clays (for example, kaolin, bentonite, acid clay, etc.), talcs (for example, talc, pyrophillite, etc.), silicas (for example, diatomaceous earth, quartz sand, mica, white carbon (fine hydrated silicon, also referred to as silicic acid hydrate, which contains high-dispersion silicic acid; some products contain mainly calcium silicate), activated carbon, sulfur powder, pumice stone, calcined diatomaceous earth, brick pulverization product, fly ash and sand, inorganic mineral powders such as calcium carbonate, calcium phosphate, chemical fertilizers or composts of ammonium sulfate, ammonium phosphate, ammonium nitrate, urea and ammonium chloride. These may be used singly or as mixtures of two or more of them.

The liquid carrier includes one having itself a solvent effect and one free from a solvent effect but can disperse the active ingredient using an adjuvant. Typical examples include the following carriers, which can be used singly or as mixtures of two or more of them, for example, water, alcohols (for example, methanol, ethanol, isopropanol, butanol, ethylene glycol, etc.), ketones (for example, acetone, methyl ethyl ketone, methyl isobutyl ketone, diisobutyl ketone, cyclohexanone, etc.), ethers (for example, ethyl ether, dioxane, Cellosolve, dipropyl ether, tetrahydrofuran, etc.), aliphatic hydrocarbons (for example, kerosene, mineral oil, etc.), aromatic hydrocarbons (for example, benzene, toluene, xylene, solvent naphtha, alkylnaphthalen, etc.), halogenated hydrocarbons (for example, dichloroethane, chloroform, carbon tetrachloride, chlorinated benzene, etc.), esters (for example, ethyl acetate, phthalate, diisopropyl phthalate, dibutyl phthalate, dioctyl phthalate, etc.), amides (for example, dimethylformamide, diethylformamide, dimethylacetamide, etc.), nitriles (for example, acetonitrile, etc.), dimethyl sulfoxide, and the like.

Other adjuvants include typical adjuvants exemplified below. These adjuvants are used depending on the purpose and they can be used singly or two or more of adjuvants can be used in combination. Alternatively, no adjuvant can be used in some cases.

For the purpose of emulsification, dispersion, solubilization and/or wetting of the active ingredient compound, a surfactant is used. Examples of the surfactant include, for example, polyoxyethylene alkyl ether, polyoxyethylene alkylaryl ether, polyoxyethylene higher fatty acid ester, polyoxyethylene resin acid ester, polyoxyethylene sorbitan monolaurate, polyoxyethylene sorbitan monooleate, alkyl aryl sulfonate, naphthalenesulfonic acid condensate, ligninsulfonate, higher alcohol sulfate, etc.

The adjuvant can be used to stabilize the active ingredient compound and to adhere or bind the active ingredient compound. Examples of such an adjuvant includes casein, gelatin, starch, methyl cellulose, carboxymethylcellulose, gum Arabic, polyvinyl alcohol, wood turpentine oil, rice bran oil, bentonite, lignin sulfite liquor, etc.

The adjuvant can be used to improve fluidity of solid products. Examples of such an adjuvant is, for example, wax, stearates, alkyl phosphates, etc.

As the deflocculated for suspension products, adjuvants such as naphthalenesulfonic acid condensates, condensed phosphates, etc. can be used.

As the defoaming agent, adjuvants such as silicone oil can be used.

The amount of the active ingredient compound may be adjusted, if desired. For example, 0.01 to 50% by weight is suitable in the case of dust or granule and 0.01 to 50% by weight is also suitable in the case of emulsions and wettable powder.

In order to control various pests, the agricultural and horticultural insecticide of the present invention can be applied in an amount effective to prevent insect damages as it is or suitably diluted with or suspended in water or the like, to crops on which emergence of the pests is expected or to the place where emergence of the pests is undesirable.

The amount of the agricultural and horticultural insecticide of the present invention may vary depending on various factors such as purpose, pests to be treated, state of growth of crops, trend of emergence of pests, weather, environmental conditions, formulations, application methods, application sites and application periods. However, it may be selected suitably depending on the purpose within the range of 0.1 g to 10 kg per 10 ares as the active ingredient compound.

The agricultural and horticultural insecticide of the present invention can be used in combination with other agricultural and horticultural agents for controlling diseases insect pests in order to further extend diseases and pests, optimal controlling time or reduce doses.

Hereafter, typical examples and test examples of the present invention will be shown. However, the present invention is not limited thereto.

In the following formulations, all parts are parts by weight.

Formulation Example 1

Compound described in Tables 1, 2 or 3 50 parts

Xylene 40 parts

A mixture of polyoxyethylene nonyl phenyl ether and calcium alkylbenzenesulfonate 10 parts The above ingredients are mixed and dissolved uniformly to form an emulsion.

Formulation Example 2

Compound described in Tables 1, 2 or 3 3 parts

Clay powder 82 parts

Diatomaceous powder 15 parts

The above ingredients are mixed and pulverized uniformly to form a dust.

Formulation Example 3

Compound described in Tables 1, 2 or 3 5 parts

Powder of bentonite and clay 90 parts

Calcium ligninsulfonate 5 parts

The above ingredients are mixed uniformly and kneaded after addition of a suitable amount of water and, the mixture was granulated and dried to obtain granules.

Formulation Example 4

Compound described in Tables 1, 2 or 3 20 parts

Kaolin and synthetic highly dispersed silicic acid 75 parts

A mixture of polyoxyethylene nonyl phenyl ether and calcium alkylbenzenesulfonate 5 parts The above ingredients are mixed and pulverized uniformly to obtain a wettable powder.

Test Example 1

Insecticidal Effect Against Diamondback Moth (*Plutella xylostella*)

On a seedling of a Chinese cabbage was left to adult of diamondback moth (*Plutella xylostella*) for breeding and allowed to lay eggs and two days after the start of breeding, the seedling of a Chinese cabbage on which the eggs are deposited was dipped in a chemical liquid prepared by diluting a chemical agent containing a compound described in Table 1, Table 2 or Table 3 to 500 ppm for 30 seconds. After air drying, the seedling was left to stand in a thermostatic chamber at 25° C. After 6 days from the dipping in the chemical solution, the number of hatched insects was examined. The mortality of insects was calculated by the following formula and determination was made according to the following standards. 1 Lot, 10 insects, 3 series system.

Corrected insect mortality (%)

Number of hatched insects of no treatment lot−number of hatched insects of treated lot=Number of hatched insects of no treated lot Standards of determination:

A: Dead insect ratio 100%

B: Dead insect ratio 99 to 90%

C: Dead insect ratio 89 to 80%

D: Dead insect ratio 79 to 50%

The results obtained are shown in Table 5.

Test Example 2

Insecticidal Effect Against Smaller Tea Tortrix (Adoxophyes sp.)

Tea leaves (variety: Yabukita) were dipped in a chemical liquid prepared by diluting a chemical agent containing a compound described in Table 1, Table 2 or Table 3 to 500 ppm for 30 seconds. After air drying, they were placed in a plastic dish of 9 cm in diameter, in which 2nd instar larvae of smaller tea tortrix (Adoxophyes sp.) were inoculated. Thereafter, the dish was covered with a lid and left to stand a thermostatic chamer at 25° C. and at a humidity of 70%. After 8 days from the inoculation, the mortality number of the insects were examined and determination was made in accordance with the Test Example 1. 1 Lot, 10 insects, 3 series system.

The results obtained are shown in Table 5.

TABLE 5

| Compound No. | Test Example 1 | Test Example 2 | Compound No. | Test Example 1 | Test Example 2 |
|---|---|---|---|---|---|
| 2 | A | A | 49 | B | |
| 3 | | A | 52 | A | A |
| 12 | | A | 53 | A | A |
| 13 | A | A | 54 | | A |
| 14 | A | A | 55 | | A |
| 21 | A | A | 57 | A | A |
| 22 | | A | 60 | A | A |
| 23 | A | A | 62 | A | A |
| 24 | A | A | 64 | A | A |
| 25 | | A | 66 | A | A |
| 26 | A | A | 67 | A | D |
| 27 | A | | 68 | | A |
| 28 | A | A | 69 | A | A |
| 29 | | A | 73 | A | A |
| 30 | A | A | 74 | A | A |
| 41 | A | A | 75 | A | A |
| 42 | A | | 76 | | A |
| 46 | A | | 77 | | A |
| 48 | A | A | 79 | A | A |
| 80 | A | A | 141 | A | A |
| 81 | A | A | 143 | A | A |
| 83 | A | A | 146 | A | A |
| 84 | B | | 147 | A | A |
| 91 | | A | 148 | A | A |
| 92 | A | A | 149 | A | A |
| 94 | A | A | 150 | A | A |
| 95 | A | A | 151 | A | A |

TABLE 5-continued

| Compound No. | Test Example 1 | Test Example 2 | Compound No. | Test Example 1 | Test Example 2 |
|---|---|---|---|---|---|
| 96 | A | A | 153 | A | A |
| 97 | A | A | 156 | A | A |
| 100 | A | A | 157 | A | A |
| 105 | A | A | 163 | | A |
| 108 | | A | 165 | A | A |
| 114 | A | A | 173 | A | A |
| 116 | A | A | 174 | | A |
| 118 | | C | 176 | | A |
| 121 | A | A | 184 | | A |
| 122 | A | A | 186 | A | A |
| 123 | A | A | 188 | A | A |
| 124 | A | A | 187 | A | A |
| 126 | A | A | 189 | A | A |
| 128 | | A | 190 | A | A |
| 191 | A | A | 245 | | A |
| 195 | A | A | 253 | A | A |
| 196 | A | A | 269 | A | A |
| 197 | | A | 270 | A | A |
| 200 | A | A | 271 | | A |
| 207 | A | A | 278 | | A |
| 209 | A | A | 279 | A | A |
| 220 | A | A | 280 | | A |
| 221 | | A | 282 | A | A |
| 223 | | A | 283 | A | C |
| 224 | | A | 284 | | A |
| 229 | A | A | 285 | A | A |
| 231 | | A | 286 | | A |
| 232 | A | A | 293 | A | A |
| 233 | A | A | 294 | A | A |
| 234 | | C | 296 | A | |
| 235 | A | A | 299 | | A |
| 236 | A | A | 306 | A | A |
| 237 | A | A | 307 | | A |
| 238 | A | A | 309 | A | A |
| 243 | A | A | 310 | A | A |
| 244 | | A | 311 | A | A |
| 312 | A | A | 350 | | A |
| 313 | A | A | 351 | | A |
| 314 | | A | 353 | | A |
| 316 | A | A | 354 | | A |
| 317 | | A | 355 | | A |
| 318 | A | A | 356 | | A |
| 319 | A | A | 359 | | A |
| 320 | | A | 362 | | A |
| 321 | A | A | 363 | | A |
| 322 | | A | 366 | A | A |
| 324 | | A | 369 | A | A |
| 325 | | A | | | |
| 326 | | A | | | |
| 327 | | A | | | |
| 328 | A | A | | | |
| 333 | | A | | | |
| 336 | A | A | | | |
| 337 | | A | | | |
| 339 | | A | | | |
| 342 | A | A | | | |
| 348 | | A | | | |
| 349 | | A | | | |

What is claimed is:

1. An aminoacetonitrile derivative of the formula (I):

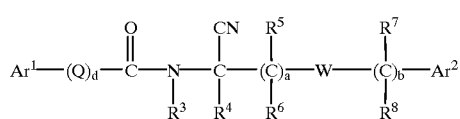

(I)

(wherein $Ar^1$ and $Ar^2$ may be the same or different and each represents a phenyl group;

a substituted phenyl group having at least one substituent which may be the same or different and selected from the group of a halogen atom, a nitro group, a cyano group, a $C_1$–$C_6$ alkyl group, a halo $C_1$–$C_6$ alkyl group, a $C_1$–$C_6$ alkoxy group, a halo $C_1$–$C_6$ alkoxy group, a $C_2$–$C_6$ alkenyl group, a halo $C_2$–$C_6$ alkenyl group, a $C_2$–$C_6$ alkynyl group, a $C_3$–$C_6$ cycloalkyl group, a $C_2$–$C_6$ alkenyloxy group, a halo $C_2$–$C_6$ alkenyloxy group, a $C_1$–$C_6$ alkylthio group, a halo $C_1$–$C_6$ alkylthio group, a $C_1$–$C_6$ alkylsulfonyloxy group, a halo $C_1$–$C_6$ alkylsulfonyloxy group, a $C_1$–$C_6$ alkylsulfinyl group, a halo $C_1$–$C_6$ alkylsulfinyl group, a $C_1$–$C_6$ alkylsulfonyl group, a halo $C_1$–$C_6$ alkylsulfonyl group, a $C_2$–$C_6$ alkenylthio group, a halo $C_2$–$C_6$ alkenylthio group, a $C_2$–$C_6$ alkenylsulfinyl group, a halo $C_2$–$C_6$ alkenylsulfinyl group, a $C_2$–$C_6$ alkenylsulfonyl group, a halo $C_2$–$C_6$ alkenylsulfonyl group, a $C_1$–$C_6$ alkylamino group, a di-$C_1$–$C_6$ alkylamino group, a $C_1$–$C_6$ alkylsulfonylamino group, a halo $C_1$–$C_6$ alkylsulfonylamino group, a $C_1$–$C_6$ alkylcarbonyl group, a halo $C_1$–$C_6$ alkylcarbonyl group, a $C_1$–$C_6$ alkyloxycarbonyl group, a phenyl group, a substituted phenyl group having at least one substituent which may be the same or different and selected from the group consisting of a halogen atom, a cyano group, a nitro group, a $C_1$–$C_6$ alkyl group, a halo $C_1$–$C_6$ alkyl group, a $C_1$–$C_6$ alkoxy group, a halo $C_1$–$C_6$ alkoxy group, a $C_1$–$C_6$ alkylthio group, a halo $C_1$–$C_6$ alkylthio group, a $C_1$–$C_6$ alkylsulfinyl group, a halo $C_1$–$C_6$ alkylsulfinyl group, a $C_1$–$C_6$ alkylsulfonyl group and a halo $C_1$–$C_6$ alkylsulfonyl group, a phenyloxy group, a substituted phenyloxy group having on the ring thereof at least one substituent which may be the same or different and selected from the group consisting of a halogen atom, a cyano group, a nitro group, a $C_1$–$C_6$ alkyl group, a halo $C_1$–$C_6$ alkyl group, a $C_1$–$C_6$ alkoxy group, a halo $C_1$–$C_6$ alkoxy group, a $C_1$–$C_6$ alkylthio group, a halo $C_1$–$C_6$ alkylthio group, a $C_1$–$C_6$ alkylsulfinyl group, a halo $C_1$–$C_6$ alkylsulfinyl group, a $C_1$–$C_6$ alkylsulfonyl group and a halo $C_1$–$C_6$ alkylsulfonyl group, a phenylacetylene group, or a substituted phenylacetylene group having on the ring thereof at least one substituent which may be the same or different and selected from the group consisting of a halogen atom, a cyano group, a nitro group, a $C_1$–$C_6$ alkyl group, a halo $C_1$–$C_6$ alkyl group, a $C_1$–$C_6$ alkoxy group,
a halo $C_1$–$C_6$ alkoxy group, a $C_1$–$C_6$ alkylthio, group,
a halo $C_1$–$C_6$ alkylthio group, a $C_1$–$C_6$ alkylsulfinyl group,
a halo $C_1$–$C_6$ alkylsulfinyl group,
a $C_1$–$C_6$ alkylsulfonyl group and
a halo $C_1$–$C_6$ alkylsulfonyl group,
a pyridyloxy group and
a substituted pyridyloxy group having on the ring thereof at least one substituent which may be the same or different and selected from the group consisting of a halogen atom, a cyano group, a nitro group, a $C_1$–$C_6$ alkyl group,
a halo $C_1$–$C_6$ alkyl group, a $C_1$–$C_6$ alkoxy group,
a halo $C_1$–$C_6$ alkoxy group, a $C_1$–$C_6$ alkylthio group,
a halo $C_1$–$C_6$ alkylthio group, a $C_1$–$C_6$ alkylsulfinyl group,
a halo $C_1$–$C_6$ alkylsulfinyl group,
a $C_1$–$C_6$ alkylsulfonyl group and
a halo $C_1$–$C_6$ alkylsulfonyl group;
Q represents a group of

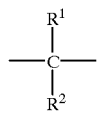

(wherein $R^1$ and $R^2$ may be the same or different and each represent a hydrogen atom, a halogen atom, a $C_1$–C6 alkyl group, a halo $C_1$–$C_6$ alkyl group, a $C_1$–$C_6$ alkoxy group, a halo $C_1$–$C_6$ alkoxy group, a $C_3$–$C_6$ cycloalkyl group, or a substituted $C_3$–$C_6$ cycloalkyl group having at least one substituent which may be the same or different and selected from the group consisting of a halogen atom and a $C_1$–$C_6$ alkyl group, and $R_1$ and $R_2$ may be bound to represent a $C_2$–$C_6$ alkylene group which may have on its chain at least one substituent selected from the group consisting of a halogen atom, a $C_1$–$C_6$ alkyl group and a $C_1$–$C_6$ alkoxy group), —CH=CH— or —C≡C—; d is 0 or an integer of 1;
$R_3$ represents a hydrogen atom, a $C_1$–$C_6$ alkyl group, a halo $C_1$–$C_6$ alkyl group, a cyano $C_1$–$C_6$ alkyl group, a $C_1$–$C_6$ alkylthio group, a halo $C_1$–$C_6$ alkylthio group, a $C_2$–$C_6$ alkenyl group or a $C_2$–$C_6$ alkynyl group;
$R_4$, $R_5$, $R_6$, $R_7$ and $R_8$ which may be the same or different and each represents a hydrogen atom, a halogen atom, a $C_1$–$C_6$ alkyl group, a halo $C_1$–$C_6$ alkyl group, a $C_3$–$C_6$ cycloalkyl group, a substituted $C_3$–$C_6$ cycloalkyl group having at least one substituent which may be the same or different and selected from the group consisting of a halogen atom and a $C_1$–$C_6$ alkyl group, a phenyl group or a substituted phenyl group having at least one substituent group which may be the same or different and selected from the group consisting of a halogen atom, a nitro group, a cyano group, a $C_1$–$C_6$ alkyl group, a halo $C_1$–$C_6$ alkyl group, a $C_1$–$C_6$, alkoxy group, a halo $C_1$–$C_6$ alkoxy group, a $C_1$–$C_6$ alkylthio group, a halo $C_1$–$C_6$ alkylthio group, a $C_1$–$C_6$ alkylsulfinyl group, a halo $C_1$–$C_6$ alkylsulfinyl group, a $C_1$–$C_6$ alkylsulfonyl group, a halo $C_1$–$C_6$ alkylsulfonyl group, a $C_1$–$C_6$ alkylamino group and a di-$C_1$–$C_6$ alkylamino group, and $R_4$ and $R_6$ together may form a $C_1$–$C_6$ alkylene group;

W is —O—, —S—, —$SO_2$,—, or —N($R^9$)— (wherein $R^9$ is a hydrogen atom or a $C_1$–$C_6$ alkyl group), and
a and b may be the same or different and a is an integer from 1 to 4 and b is 0 or an integer from 1 to 4)).
2. An aminoacetonitrile derivative as claimed in claim 1, wherein $Ar^1$ and $Ar^2$ represent a phenyl group;
a substituted phenyl group having at least one substituent which may be the same or different and selected from the group of
a halogen atom, a cyano group, a nitro group,
a $C_1$–$C_6$, alkyl group, a halo $C_1$–$C_6$ alkyl group,
a $C_2$–$C_6$ alkenyl group, a halo $C_2$–$C_6$, alkenyl group,
a $C_2$–$C_6$ alkynyl group, a $C_3$–$C_6$ cycloalkyl group,
a C1–C6 alkoxy group, a halo $C_1$–$C_6$ alkoxy group,
a $C_2$–$C_6$ alkenyloxy group, a halo $C_2$–$C_6$ alkenyloxy group,
a $C_1$–$C_6$ alkylsulfonyloxy group,
a halo $C_1$–$C_6$, alkylsulfonyloxy group,
a $C_1$–$C_6$ alkylthio group, a halo $C_1$–$C_6$ alkylthio group,
a $C_1$–$C_6$ alkylsulfinyl group,
a halo $C_1$–$C_6$ alkylsulfinyl group,
a $C_1$–$C_6$ alkylsulfonyl group,
a halo $C_1$–$C_6$, alkylsulfonyl group,
a $C_2$–$C_6$ alkenylthio group,
a halo $C_2$–$C_6$ alkenylthio group,
a $C_2$–$C_6$ alkenylsulfinyl group,
a halo $C_2$–$C_6$ alkenylsulfinyl group,
a $C_2$–$C_6$ alkenylsulfonyl group,
a halo $C_2$–$C_6$ alkenylsulfonyl group,
a $C_1$–$C_6$ alkylamino group, a di-$C_1$–$C_6$ alkylamino group,
a $C_1$–$C_6$ alkylsulfonylamino group,
a halo $C_1$–$C_6$ alkylsulfonylamino group,
a $C_1$–$C_6$ alkylcarbonyl group,
a halo $C_1$–$C_6$ alkylcarbonyl group,
a $C_1$–$C_6$ alkyloxycarbonyl group,
a phenyl group,
a substituted phenyl group having at least one substituent which may be the same or different and selected from the group consisting of a halogen atom, a cyano group, a nitro group,
a halo $C_1$–$C_6$ alkyl group, a halo $C_1$–$C_6$ alkoxy group,
a halo $C_1$–$C_6$ alkylsulfonyloxy group,
a halo $C_1$–$C_6$ alkylthio group,
a halo $C_1$–$C_6$ alkylsulfinyl group and
a halo $C_1$–$C_6$ alkylsulfonyl group,
a phenyloxy group,
a substituted phenyloxy group having on the ring thereof at least one substituent which may be the same or different and selected from the group consisting of a halogen atom,
a cyano group, a nitro group, a halo $C_1$–$C_6$ alkyl group,
a halo $C_1$–$C_6$ alkoxy group, a halo $C_1$–$C_6$ alkylthio group,
a halo $C_1$–$C_6$ alkylsulfinyl group and
a halo $C_1$–$C_6$ alkylsulfonyl group,
a phenylacetylene group, or
a substituted phenylacetylene group having on the ring thereof at least one substituent which may be the same or different and selected from the group consisting of a halogen atom, a cyano group, a nitro group, a $C_1$–$C_6$ alkyl group, a halo $C_1$–$C_6$ alkyl group, a $C_1$–$C_6$ alkoxy group"
a halo $C_1$–$C_6$ alkoxy group, a $C_1$–$C_6$ alkylthio group,
a halo $C_1$–$C_6$ alkylthio group, a $C_1$–$C_6$ alkylsulfinyl group,
a halo $C_1$–$C_6$ alkylsulfinyl group,
$C_1$–$C_6$ alkylsulfonyl group and
a halo $C_1$–$C_6$ alkylsulfonyl group,
a pyridyloxy group, and
a substituted pyridyloxy group having on the ring thereof at least one substituent which may be the same or different and selected from the group consisting of a halogen atom,
a cyano group, a nitro group, a halo $C_1$–$C_6$ alkyl group, a halo $C_1$–$C_6$ alkoxy group, a halo $C_1$–$C_6$ alkylthio group,
a halo $C_1$–$C_6$ alkylsulfinyl group and
a halo $C_1$–$C_6$ alkylsulfonyl group;
Q represents a group of

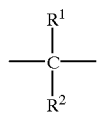

(wherein $R_1$ and $R_2$ may be the same or different and each represent a hydrogen atom, a halogen atom, a $C_1$–$C_6$ alkyl group,
a halo $C_1$–$C_6$ alkyl group or a $C_1$–$C_6$ alkoxy group, and $R_1$ and $R_2$ may be bound to represent a $C_2$–$C_6$ alkylene group which may have on its chain at least one substituent selected from the group consisting of a halogen atom, a $C_1$–$C_6$ alkyl group or a $C_1$–$C_6$, alkoxy group), —CH═CH— or —C≡C—; d is 0 or an integer of 1;
$R_3$ represents a hydrogen atom, a $C_1$–$C_6$, alkyl group, a halo $C_1$–$C_6$ alkyl group, a $C_2$–$C_6$ alkenyl group or a $C_2$–$C_6$ alkynyl group;
$R_4$, $R_5$, $R_6$, $R_7$ and $R_8$ which may be the same or different and each represents a hydrogen atom, a $C_1$–$C_6$ alkyl group, a halo $C_3$–$C_6$, alkyl group, a $C_3$–$C_6$ cycloalkyl group, or a substituted $C_3$–$C_6$ cycloalkyl group having at least one substituent which may be the same or different and selected from the group consisting of a halogen atom and a $C_1$–$C_6$, alkyl group, and $R_4$ and $R_5$ together may form a $C_1$–$C_6$ alkylene group;
W is —O—, —S—, —SO2— or —N($R_9$)— (wherein $R_9$ is a hydrogen atom or a $C_1$–$C_6$, alkyl group), and
a and b may be the same or different and a is an integer from 1 to 4 and b is 0 or an integer from 1 to 4)).
3. An aminoacetonitrile derivative as claimed in claim 2, wherein $Ar^1$ and $Ar^2$ represent a phenyl group;
a substituted phenyl group having at least one substituent which may be the same or different and selected from the group of
a halogen atom, a cyano group, a nitro group,
a $C_1$–$C_6$ alkyl group, a halo $C_1$–$C_6$ alkyl group,
a $C_1$–$C_6$ alkoxy group, a halo $C_1$–$C_6$ alkoxy group,
a $C_1$ $C_6$ alkenyloxy group, a halo $C_2$–$C_6$ alkenyloxy group,
a $C_1$–$C_6$ alkylthio group, a halo $C_1$–$C_6$ alkylthio group,
a $C_1$–$C_6$ alkylsulfonyl group,
a halo $C_1$–$C_6$ alkylsulfonyl group,
a $C_2$–$C_6$ alkenylthio group,
a halo $C_2$–$C_6$ alkenylthio group,
a $C_2$–$C_6$ alkenylsulfonyl group,
a halo $C_2$–$C_6$ alkenylsulfonyl group,
a $C_1$–$C_6$ alkyloxycarbonyl group,
a phenyl group,
a substituted phenyl group having at least one substituent which may be the same or different and selected from the group consisting of a halogen atom, a cyano group, a nitro group,
a halo $C_1$–$C_6$ alkyl group, a halo $C_1$–$C_6$ alkoxy group,
a halo $C_1$–$C_6$ alkylthio group and
a halo $C_1$–$C_6$ alkylsulfonyl group,
a phenyloxy group,
a substituted phenyloxy group having on the ring thereof at least one substituent which may be the same or different and selected from the group consisting of a halogen atom, a cyano group, a nitro group, a halo $C_1$–$C_6$ alkyl group, a halo $C_1$–$C_6$ alkoxy group, a halo $C_1$–$C_6$ alkylthio group and a halo $C_1$–$C_6$ alkylsulfonyl group,
a phenylacetylene group, or
a substituted phenylacetylene group having on the ring thereof at least one substituent which may be the same or different and selected from the group consisting of a halogen atom, a cyano group, a nitro group, a halo $C_1$–$C_6$ alkyl group, a halo $C_1$–$C_6$ alkoxy group, a halo $C_1$–$C_6$ alkylthio group and a halo $C_1$–$C_6$ alkylsulfonyl group,
Q represents a group of
(wherein $R_1$ and $R_2$ may be the same or different and each represent a hydrogen atom, a halogen atom, a $C_1$–$C_6$ alkyl group,
a halo $C_1$–$C_6$, alkyl group or a $C_1$–$C_6$ alkoxy group, and $R^1$ and $R^2$ may be bound to represent a $C_2$–$C_6$ alkylene group which may have on its chain at least one substituent selected from the group consisting of a halogen atom, a $C_1$–$C_6$ alkyl group and a $C_1$–$C_6$ alkoxy group), —CH═CH— or —C≡C—; d is 0 or an integer of 1;
$R^3$ represents a hydrogen atom, a C,—C, alkyl group, a halo $C_1$–$C_6$ alkyl group, a $C_2$–$C_6$ alkenyl group or a $C_2$–$C_6$ alkynyl group;
$R^4$, $R^5$, $R^6$, $R^7$ and $R^8$ which may be the same or different and each represents a hydrogen atom, a $C_1$–$C_6$ alkyl group, a halo $C_1$–$C_6$ alkyl group, a $C_3$–$C_6$ cycloalkyl group or a substituted $C_3$–$C_6$ cycloalkyl group having at least one substituent which may be the same or different and selected from the group consisting of a halogen atom and a $C_1$–$C_6$ alkyl group, and $R^4$ and $R^5$ together may form a $C_1$–$C_6$ alkylene group;
W is —O—, —S—, —SO$_2$— or —N($R^9$)— (wherein $R^9$ is a hydrogen atom or a $C_1$–$C_6$ alkyl group), and
a and b may be the same or different and a is an integer from 1 to 4 and b is 0 or an integer from 1 to 4)).
4. An agricultural and horticultural pesticide composition containing as an active ingredient the aminoacetonitrile derivative as claimed in claim 3.
5. A method of combating pests using an agricultural and horticultural pesticide, the method comprising applying an effective amount of the agricultural and horticultural pesticide composition as claimed in claim 4 to useful plants for the protection of the useful plants.
6. The aminoacetonitrile derivative of claim 1, wherein $Ar^1$ and $Ar^2$ may be the same or different and each represents a phenyl group.

7. The aminoacetonitrile derivative of claim 1, wherein $Ar^1$ and $Ar^2$ may be the same or different and each represents a substituted phenyl group having at least one substituent which may be the same or different and selected from the group of
- a halogen atom, a nitro group, a cyano group,
- a $C_1$–$C_6$ alkyl group, a halo $C_1$–$C_6$ alkyl group,
- a $C_1$–$C_1$ alkoxy group, a halo $C_1$–$C_1$ alkoxy group,
- a $C_2$–$C_6$ alkenyl group, a halo $C_2$–$C_6$ alkenyl group,
- a $C_2$–$C_6$ alkynyl group, a $C_3$–$C_6$ cycloalkyl group,
- a $C_2$–$C_6$ alkenyloxy group, a halo $C_2$–$C_6$ alkenyloxy group,
- a $C_1$–$C_6$ alkylthio group, a halo $C_1$–$C_6$ alkylthio group,
- a $C_1$–$C_6$ alkylsulfonyloxy group,
- a halo $C_1$–$C_6$ alkylsulfonyloxy group,
- a $C_1$–$C_6$ alkylsulfinyl group,
- a halo $C_1$–$C_6$ alkylsulfinyl group,
- a $C_1$–$C_6$ alkylsulfonyl group,
- a halo $C_1$–$C_6$ alkylsulfonyl group,
- a $C_2$–$C_6$ alkenylthio group,
- a halo $C_2$–$C_6$ alkenylthio group,
- a $C_2$–$C_6$ alkenylsulfinyl group,
- a halo $C_2$–$C_6$ alkenylsulfinyl group,
- a $C_2$–$C_6$ alkenylsulfonyl group,
- a halo $C_2$–$C_6$ alkenylsulfonyl group,
- a $C_1$–$C_6$ alkylamino group, a di-$C_1$–$C_6$ alkylamino group,
- a $C_1$–$C_6$ alkylsulfonylamino group,
- a halo $C_1$–$C_6$ alkylsulfonylamino group,
- a $C_1$–$C_6$ alkylcarbonyl group,
- a halo $C_1$–$C_6$ alkylcarbonyl group,
- a $C_1$–$C_6$ alkyloxycarbonyl group,
- a phenyl group,
- a substituted phenyl group having at least one substituent which may be the same or different and selected from the group consisting of a halogen atom, a cyano group,
- a nitro group, a $C_1$–$C_6$ alkyl group,
- a halo $C_1$–$C_6$ alkyl group, a $C_1$–$C_6$ alkoxy group,
- a halo $C_1$–$C_6$ alkoxy group, a $C_1$–$C_1$ alkylthio group,
- a halo $C_1$–$C_6$ alkylthio group, a $C_1$–$C_6$ alkylsulfinyl group,
- a halo $C_1$–$C_6$ alkylsulfinyl group,
- a $C_1$–$C_1$ alkylsulfonyl group and
- a halo $C_1$–$C_6$ alkylsulfonyl group.

8. The aminoacetonitrile derivative of claim 1, wherein $Ar^1$ and $Ar^2$ may be the same or different and each represents a phenyloxy group.

9. The aminoacetonitrile derivative of claim 1, wherein $Ar^1$ and $Ar^2$ may be the same or different and each represents a substituted phenyloxy group having on the ring thereof at least one substituent which may be the same or different and selected from the group consisting of a halogen atom, a cyano group, a nitro group,
- a $C_1$–$C_6$ alkyl group, a halo $C_1$–$C_6$ alkyl group,
- a $C_1$–$C_6$ alkoxy group, a halo $C_1$–$C_6$ alkoxy group,
- a $C_1$–$C_6$ alkylthio group, a halo $C_1$–$C_6$ alkylthio group,
- a $C_1$–$C_6$ alkylsulfinyl group,
- a halo $C_1$–$C_6$ alkylsulfinyl group,
- a $C_1$–$C_6$ alkylsulfonyl group and
- a halo $C_1$–$C_6$ alkylsulfonyl group.

10. The aminoacetonitrile derivative of claim 1, wherein $Ar^1$ and $Ar^2$ may be the same or different and each represents a phenylacetylene group.

11. The aminoacetonitrile derivative of claim 1, wherein $Ar^1$ and $Ar^2$ may be the same or different and each represents a substituted phenylacetylene group having on the ring thereof at least one substituent which may be the same or different and selected from the group consisting of a halogen atom, a cyano group, a nitro group, a $C_1$–$C_6$ alkyl group,
- a halo $C_1$–$C_6$ alkyl group, a $C_1$–$C_6$ alkoxy group,
- a halo $C_1$–$C_6$ alkoxy group, a $C_1$–$C_6$ alkylthio, group,
- a halo $C_1$–$C_6$ alkylthio group, a $C_1$–$C_6$ alkylsulfinyl group,
- a halo $C_1$–$C_6$ alkylsulfinyl group,
- a $C_1$–$C_6$ alkylsulfonyl group and
- a halo $C_1$–$C_6$ alkylsulfonyl group,
- a pyridyloxy group and
- a substituted pyridyloxy group having on the ring thereof at least one substituent which may be the same or different and selected from the group consisting of a halogen atom, a cyano group, a nitro group, a $C_1$–$C_6$ alkyl group,
- a halo $C_1$–$C_6$ alkyl group, a $C_1$–$C_6$ alkoxy group,
- a halo $C_1$–$C_6$ alkoxy group, a $C_1$–$C_6$ alkylthio group,
- a halo $C_1$–$C_6$ alkylthio group, a $C_1$–$C_6$ alkylsulfinyl group,
- a halo $C_1$–$C_6$ alkylsulfinyl group,
- a $C_1$–$C_6$ alkylsulfonyl group and
- a halo $C_1$–$C_6$ alkylsulfonyl group.

* * * * *